United States Patent
Oster et al.

(10) Patent No.: US 11,452,877 B2
(45) Date of Patent: Sep. 27, 2022

(54) METHODS OF SHIELDING IMPLANTABLE MEDICAL LEADS AND IMPLANTABLE MEDICAL LEAD EXTENSIONS

(71) Applicant: MEDTRONIC, INC., Minneapolis, MN (US)

(72) Inventors: Daniel C. Oster, Minneapolis, MN (US); Jonathan P. Bogott, Crystal, MN (US); Michael J. Schendel, Andover, MN (US); Nathan A. Torgerson, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 91 days.

(21) Appl. No.: 16/177,354

(22) Filed: Oct. 31, 2018

(65) Prior Publication Data
US 2019/0070410 A1 Mar. 7, 2019

Related U.S. Application Data

(62) Division of application No. 14/807,323, filed on Jul. 23, 2015, now Pat. No. 10,155,111.

(60) Provisional application No. 62/028,798, filed on Jul. 24, 2014.

(51) Int. Cl.
*A61N 1/37* (2006.01)
*A61N 1/05* (2006.01)
*A61N 1/08* (2006.01)

(52) U.S. Cl.
CPC ......... *A61N 1/3718* (2013.01); *A61N 1/0529* (2013.01); *A61N 1/0553* (2013.01); *A61N 1/086* (2017.08)

(58) Field of Classification Search
CPC ...... A61N 1/08; A61N 1/0553; A61N 1/0529; A61N 1/3718; A61N 1/086; A61F 5/0013; A61F 5/0089
USPC ........................................................ 607/116
See application file for complete search history.

(56) References Cited

U.S. PATENT DOCUMENTS

| | | | |
|---|---|---|---|
| 7,822,484 B1 * | 10/2010 | Zhao ...................... | A61N 1/056 607/116 |
| 8,543,222 B1 * | 9/2013 | Sochor ................. | A61N 1/0529 607/116 |
| 2006/0079949 A1 * | 4/2006 | Brostrom ............... | A61N 1/056 607/119 |

(Continued)

OTHER PUBLICATIONS

European Application No. 15 745 714.4, EP Office Action Communication, dated Apr. 23, 2020.

(Continued)

*Primary Examiner* — Gary Jackson
*Assistant Examiner* — Alexander M Eisenberg
(74) *Attorney, Agent, or Firm* — Withers & Keys, LLC

(57) ABSTRACT

Shielded sheaths are placed over implantable medical leads and/or implantable medical lead extensions to provide shielding from electromagnetic energy and to prevent heating at the electrodes. The shielded sheaths include insulative bodies with shield layers such as conductive braided wire or conductive foil tubular structures. The shielded sheath may be implanted at the time of implanting the lead and/or lead extension. The shielded sheath may also be implanted at a later time after the lead and/or lead extension has previously been implanted. The shielded sheath may be anchored onto the lead or lead extension.

4 Claims, 32 Drawing Sheets

(56) References Cited

U.S. PATENT DOCUMENTS

| | | | |
|---|---|---|---|
| 2008/0009914 A1* | 1/2008 | Buysman | A61N 1/05 |
| | | | 607/41 |
| 2008/0046062 A1* | 2/2008 | Camps | A61N 1/0587 |
| | | | 607/133 |
| 2008/0154326 A1 | 6/2008 | Clyne | |
| 2010/0256696 A1* | 10/2010 | Schleicher | A61N 1/0558 |
| | | | 607/2 |
| 2010/0318098 A1* | 12/2010 | Lund | A61B 17/06109 |
| | | | 606/129 |
| 2011/0112548 A1* | 5/2011 | Fifer | A61B 17/320016 |
| | | | 606/129 |
| 2012/0035590 A1* | 2/2012 | Whiting | A61B 17/3468 |
| | | | 604/528 |
| 2012/0035616 A1* | 2/2012 | Olsen | A61B 90/39 |
| | | | 606/129 |
| 2012/0046722 A1* | 2/2012 | Olsen | A61N 1/3752 |
| | | | 607/116 |
| 2013/0166007 A1* | 6/2013 | True | A61N 1/0565 |
| | | | 607/116 |
| 2013/0317518 A1* | 11/2013 | Govea | A61N 1/0551 |
| | | | 606/129 |

OTHER PUBLICATIONS

European Application No. 15 745 714.4, EP Office Action Communication, dated Dec. 15, 2020.

* cited by examiner

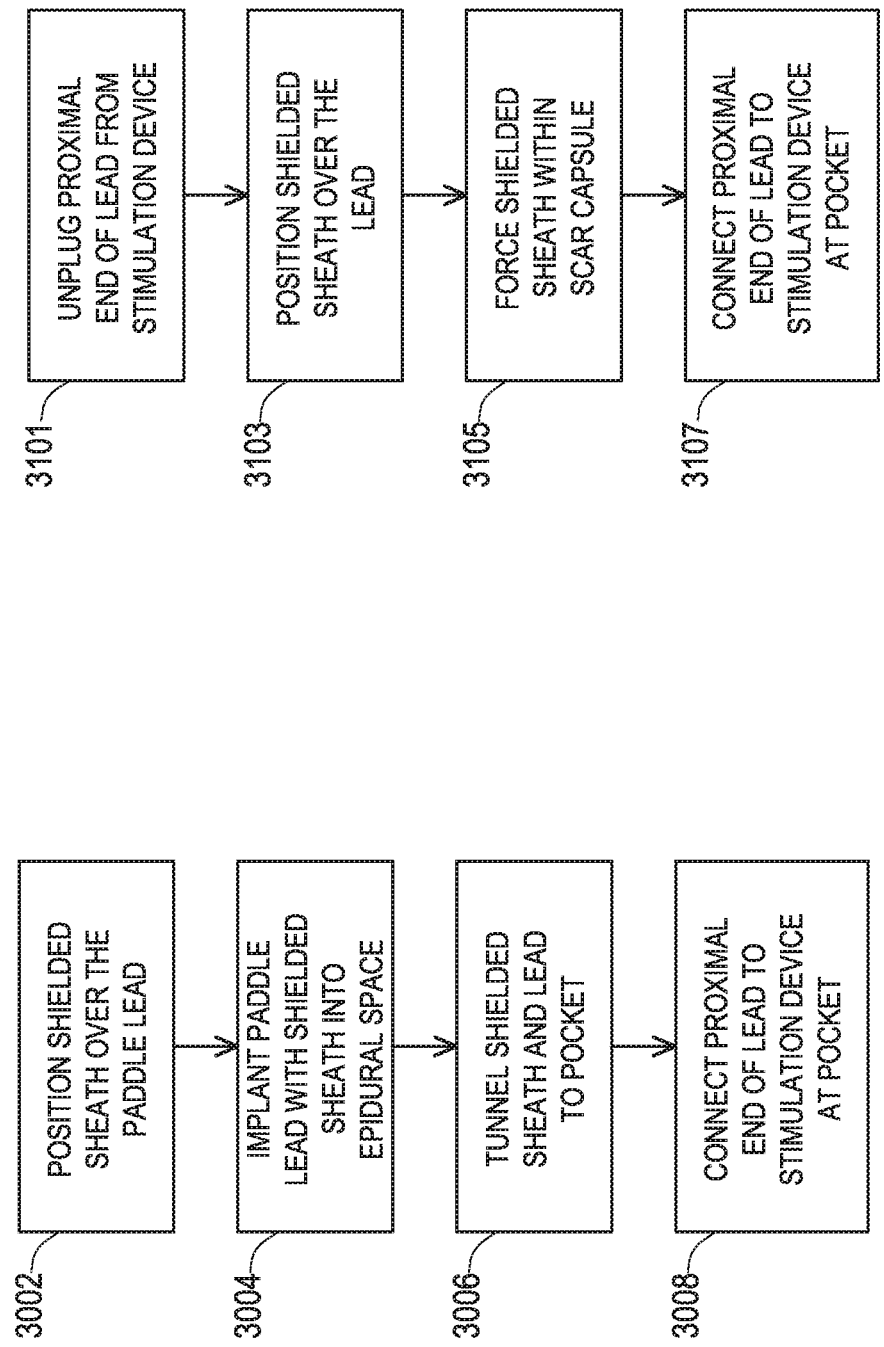

METHODS OF SHIELDING IMPLANTABLE MEDICAL LEADS AND IMPLANTABLE MEDICAL LEAD EXTENSIONS

RELATED APPLICATIONS

The present application is a divisional of U.S. application Ser. No. 14/807,323, filed on Jul. 23, 2015, which claims priority to U.S. Provisional Application No. 62/028,798, filed Jul. 24, 2014, both of which are incorporated by reference herein in their entirety.

TECHNICAL FIELD

Embodiments relate to implantable medical leads and implantable medical lead extensions. More particularly, embodiments relate to methods of shielding implantable medical leads and implantable medical lead extensions.

BACKGROUND

Implantable medical systems are used to provide stimulation therapy and/or physiological sensing for patients. The implantable medical system includes a stimulation or sensing device that is implanted at a convenient location. Implantable medical leads are routed between the site of implantation of the device and a target site where stimulation or sensing is to occur. Where the route is lengthy, an implantable medical lead extension is used to traverse a portion of that distance.

The implantable medical leads include one or more electrical contacts located near a proximal end of the lead. Where no extension is needed, the proximal end of the lead is physically connected to the stimulation or sensing device so that the proximal contacts of the lead are electrically coupled to electrical circuitry of the device. For scenarios where the implantable medical lead extension is used, then the proximal end of the lead is physically connected to a distal end of the extension where electrical connectors of the extension are coupled to the electrical contacts of the lead. The proximal end of the extension is physically connected to the stimulation or sensing device so that the proximal contacts of the extension are electrically coupled to electrical circuitry of the device. The leads also include one or more electrodes located near a distal end of the leads. Electrical conductors are present within the lead, and each electrical conductor is connected to a respective electrical contact and electrode to provide an electrical path for stimulation and/or sensed signals. Electrical conductors are also present within the extension, and each electrical conductor is connected to a respective electrical contact and distal connector to provide an electrical path for stimulation and/or sensed signals.

Because the lead and lead-extension combination extends over a significant distance within the body, each electrical conductor within the lead and extension is susceptible to receiving extraneous electromagnetic energy that produces electrical current on the electrical conductor. While most ambient conditions expose the lead and lead extension to insignificant levels of such extraneous electromagnetic energy, certain situations may create levels of extraneous electromagnetic energy that are of concern. An example of such a situation is a magnetic resonance imaging (MRI) scan. The MRI scan utilizes a high energy radio frequency (RF) electromagnetic signal. This RF signal may produce relatively large levels of electrical current on the electrical conductor of the lead and extension when the patient having the implantable medical system that includes the lead and/or lead extension combination undergoes the MRI scan. The relatively large electrical current that results from the high energy RF signal produces heating at the electrodes that may create discomfort and even dangerous tissue damage at the site within the body where the one or more electrodes of the lead are located.

It has been found that a shield layer within the lead reduces the amount of RF energy that reaches the electrical conductors, which in turn reduces the amount of current being coupled onto the electrical conductors and reduces the heating at the electrodes to acceptable levels. The manufacturing process of the lead has been altered to include a shield layer when the lead body is being manufactured by creating an inner jacket over the electrical conductor, then creating the shield layer on the inner jacket, and then creating an outer jacket over the inner jacket. The electrical contacts and electrodes are then installed about the inner jacket and are coupled to the electrical conductor to complete the leads. However, leads and extensions that have been constructed without such shield layers or other protective aspects remain vulnerable to the high levels of RF energy of the MRI scan or other situation.

Additionally, patients having leads and/or extensions implanted that are not designed to be safe during an MRI scan either continue to be ineligible for an MRI scan or must undergo a procedure to replace the lead and/or extension with an MRI compliant version. Replacing the existing lead presents a risk that the new lead will not be positioned in a location that provides therapy that is as effective as with the prior lead. Furthermore, some leads are very difficult to remove, such as leads having a distal paddle that have required surgical procedures for implantation.

SUMMARY

Embodiments address issues such as these and others by adding a shielded sheath over an existing lead or extension. The shielded sheath may then be anchored to the existing lead or extension and to the surrounding body tissue. The shielded sheath may be added to newly implanted leads and/or extensions or to leads and/or extensions that have previously been implanted.

Embodiments provide a method of shielding an implantable medical lead. The method involves providing a sheath that includes a shield layer. The method further involves positioning the sheath that includes the shield layer about an implantable medical lead between a proximal contact on the implantable medical lead and a distal electrode on the implantable medical lead. The method additionally involves anchoring the sheath to the implantable medical lead.

Embodiments provide an apparatus that includes an implantable medical lead having a proximal contact and a distal electrode and also includes a sheath containing a shield layer positioned about the implantable medical lead between the proximal contact and the distal electrode. The apparatus further includes an anchoring structure holding the sheath in a fixed position about the implantable medical lead.

Embodiments provide an implantable medical system that includes an implantable stimulation device and an implantable medical lead having a proximal contact and a distal electrode with the proximal contact being electrically coupled to the implantable stimulation device. The system further includes a sheath containing a shield layer positioned about the implantable medical lead between the proximal contact and the distal electrode and an anchoring structure holding the sheath in a fixed position about the implantable medical lead.

Embodiments provide an apparatus that includes an implantable medical lead extension having a proximal contact and a distal connector block and also includes a sheath containing a shield layer positioned about the implantable medical lead between the proximal contact and a distal end of the implantable medical lead extension. The apparatus further includes an anchoring structure holding the sheath in a fixed position about the implantable medical lead extension.

Embodiments provide a method of shielding an implantable medical paddle lead that involves providing a sheath that includes a shield layer. The method further involves positioning the sheath that includes the shield layer about an implantable medical lead between a proximal contact on the implantable medical lead and a paddle portion of the implantable medical paddle lead, the sheath having an inner diameter that is smaller than a width of the paddle portion of the paddle lead but greater than a diameter of a remainder of the paddle lead such that the sheath is confined by the paddle portion.

Embodiments provide an apparatus that includes an implantable medical paddle lead having a proximal contact and a paddle portion that contains at least one distal electrode, the paddle portion having a width greater than a remainder of the implantable medical paddle lead. The apparatus further includes a sheath containing a shield layer positioned about the implantable medical lead between the proximal contact and the paddle portion, the sheath having an inner diameter that is smaller than a width of the paddle portion of the paddle lead but greater than a diameter of a remainder of the paddle lead such that the sheath is confined by the paddle portion.

Embodiments provide an implantable medical system that includes an implantable stimulation device. The system further includes an implantable medical paddle lead having a proximal contact and a paddle portion that contains at least one distal electrode with the proximal contact being electrically coupled to the implantable stimulation device, the paddle portion having a width greater than a remainder of the implantable medical paddle lead. The system additionally includes a sheath containing a shield layer positioned about the implantable medical lead between the proximal contact and the paddle portion, the sheath having an inner diameter that is smaller than a width of the paddle portion of the paddle lead but greater than a diameter of a remainder of the paddle lead such that the sheath is confined by the paddle portion.

DESCRIPTION OF THE DRAWINGS

FIG. 30 shows a set of operations for another manner of implanting a shielded sheath and an implantable medical paddle lead.

FIGS. 31A and 31B show sets of operations for ways of implanting a shielded sheath onto a previously implanted medical paddle lead.

DETAILED DESCRIPTION

Embodiments provide shielded sheaths that are installed over leads and/or extensions, whether being implanted or already implanted. The shielded sheath reduces the amount of RF energy that reaches the conductors of the lead and/or extension.

Figure 1:
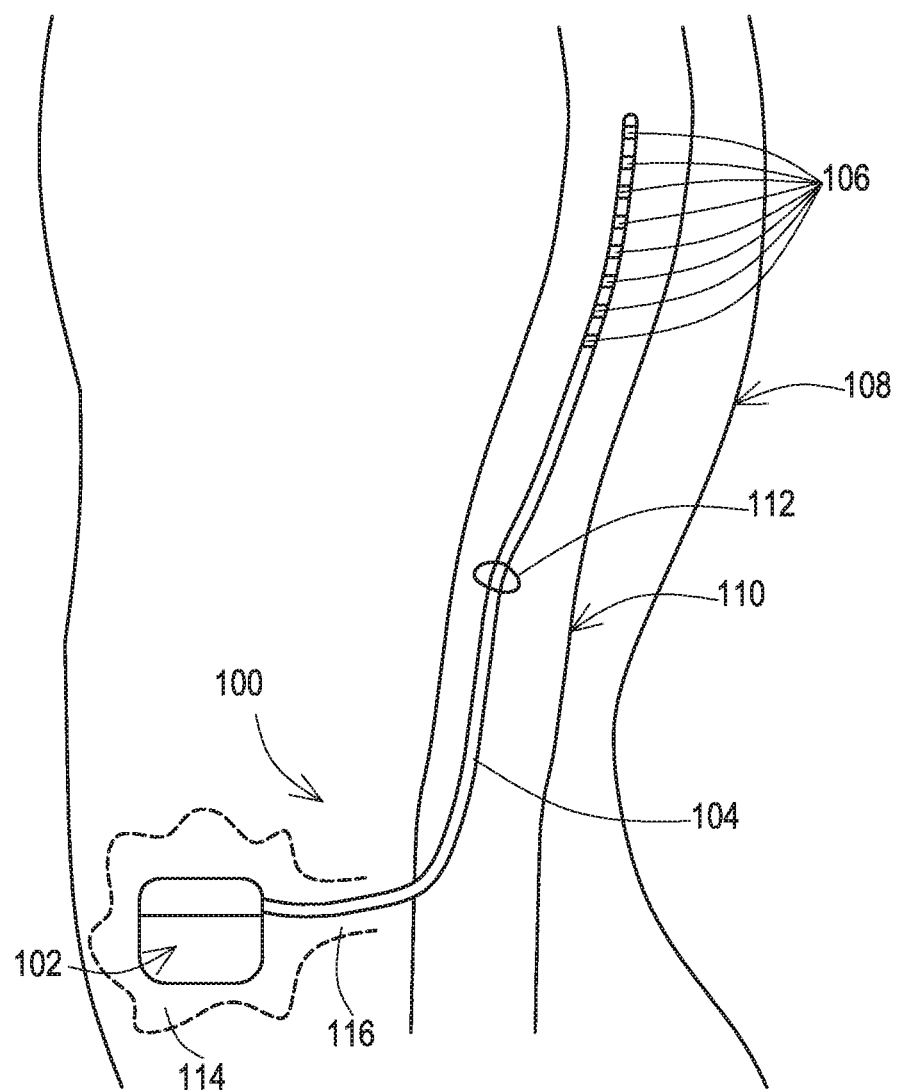
FIG. 1 shows an implantable medical system including a lead that has been implanted prior to introduction of a shielded sheath.

FIG. 1 shows an example where a shielded sheath may be utilized. An implantable medical system 100 that includes an implantable medical device 102 which may be an implantable stimulation device that provides electrical stimulation signals and/or senses physiological signals. The system 100 also includes an implantable medical lead 104 is implanted into a patient 108. In this particular example, the implantable medical system is a spinal cord stimulator where the lead 104 is implanted into a location nearby the spinal cord within the spine 110. The implantable medical device 102 provides electrical stimulation that is delivered through conductors of the lead 104 to the stimulation site. The implantable medical device 102 is implanted within a subcutaneous pocket 114 created during implantation while the lead 104 is tunneled through a path 116 created between the pocket 114 and the entry point 112 to an epidural space during implantation.

Figure 2:
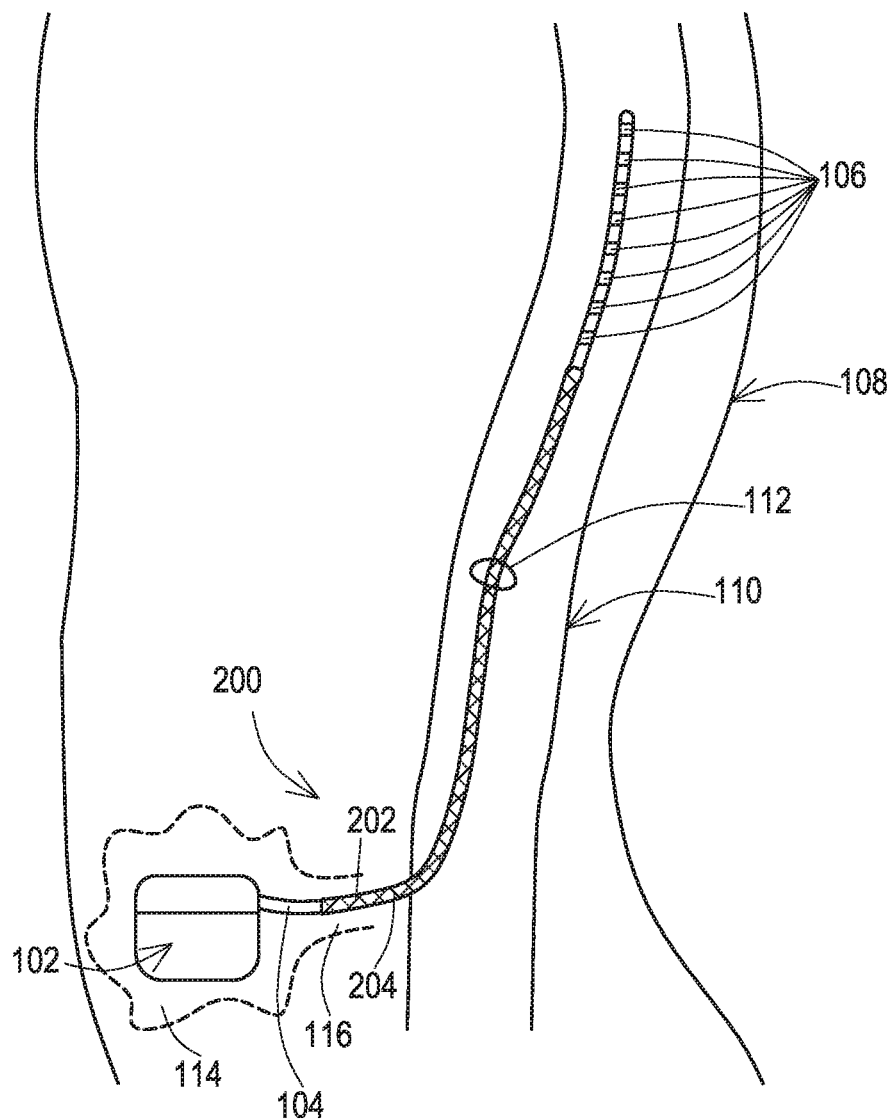
FIG. 2 shows the implantable medical system with the shielded sheath installed over the lead.

FIG. 2 shows an implantable medical system 200 which is identical to the system 100 of FIG. 1 except that a shielded sheath 202 has been placed over the lead 104. The shielded sheath is positioned between the proximal end where the lead 104 connects to the implantable medical device and the distal end where the electrodes 106 are located. The shielded sheath 202 has an insulative shield body with a shield layer 204 within the shield body to isolate the shield layer 204 from the external conditions of the body 108. The shielded sheath provides shielding of RF electromagnetic energy to reduce the amount of RF electromagnetic energy that becomes coupled to the conductors that are within the lead 104 and are connected between the implantable medical device 102 and the electrodes 106.

Figure 26:
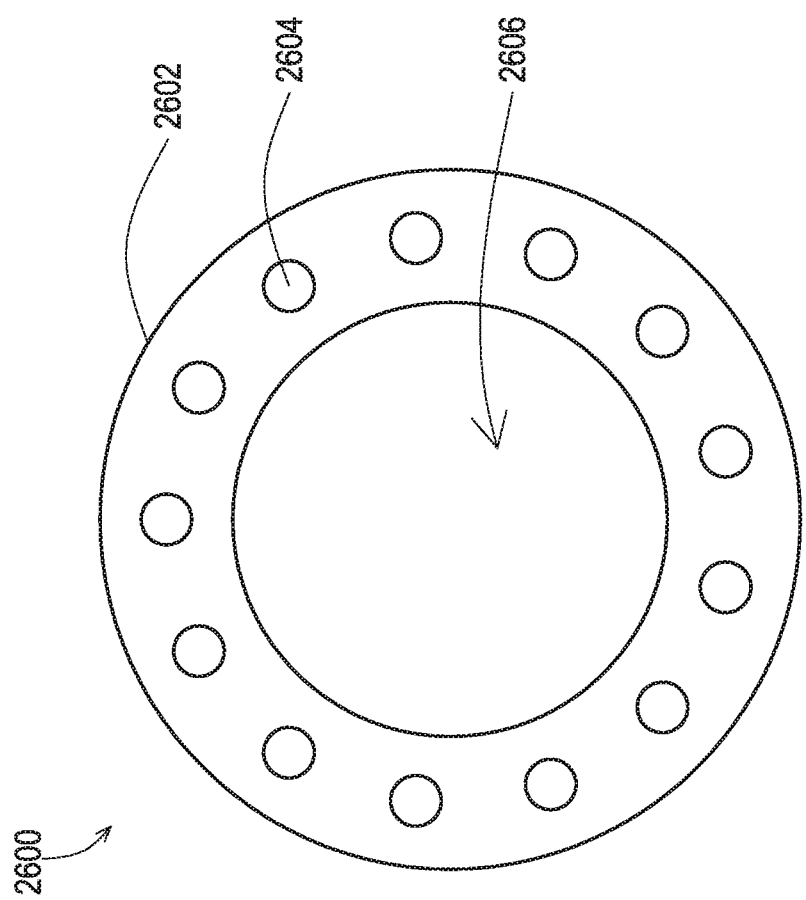
FIG. 26 shows a lateral cross-sectional view of an example of a shielded sheath.

FIG. 26 shows a lateral cross-sectional view of an example 2600 of the shielded sheath 202. In the shielded sheath 2600, there is an insulative shield body 2602 that defines a lumen 2606 where the lead 104 or a lead extension may pass through. The insulative body may be constructed of various biocompatible materials including various polymers, urethanes such as the PurSil® thermoplastic silicone-polyether-urethane of the Koninklijke DSM N.V. Corporation of the Netherlands, and other silicones. A shield layer 2604 is also present and is embedded within the insulative layer. The shield layer 204 in FIG. 2 as well as the shield layer 2604 of FIG. 26 is in the form of a tubular structure of braided conductive wires to provide a tubular braided shield layer. However, other forms of shield layers are also possible, for instance, a conductive foil tube. For a braided shield, the wires of the braid may be a conductor such as a biocompatible metal like tantalum, titanium, and the like. For a foil shield, the foil may be a conductor such as a biocompatible metal like titanium, tantalum, stainless steel, MP35N® alloy of SPS Technologies, Inc. of Jenkintown, Pa., and the like.

Where the shield layer 204 is a braided wire shield as shown in FIG. 2, the braid may be created with a variety of shield parameters. Examples of shield parameters such as braid angle, wire cross-sectional shape and diameter, number of braid wires, braid depth, distance from shield termination to closest contact or electrode, and the like that may also be used for the embodiments being disclosed herein are described in U.S. patent application Ser. No. 13/264,067, which is incorporated herein by reference in its entirety.

The shielded sheath 202 may be installed during a new implantation of the lead 104 or as a retrofit to a lead 104 that has previously been implanted. Examples of procedures for installing the shielded sheath 202 are discussed below, with the procedure for installing during a new spinal implantation of the lead 104 being described with reference to FIGS. 3-11 and the procedure for retrofitting a spinal lead 104 that has previously been implanted with reference to FIGS. 12-17. An example of a procedure for installing the shielded sheath for a brain lead is discussed below in relation to FIGS. 18-23.

Figure 3:
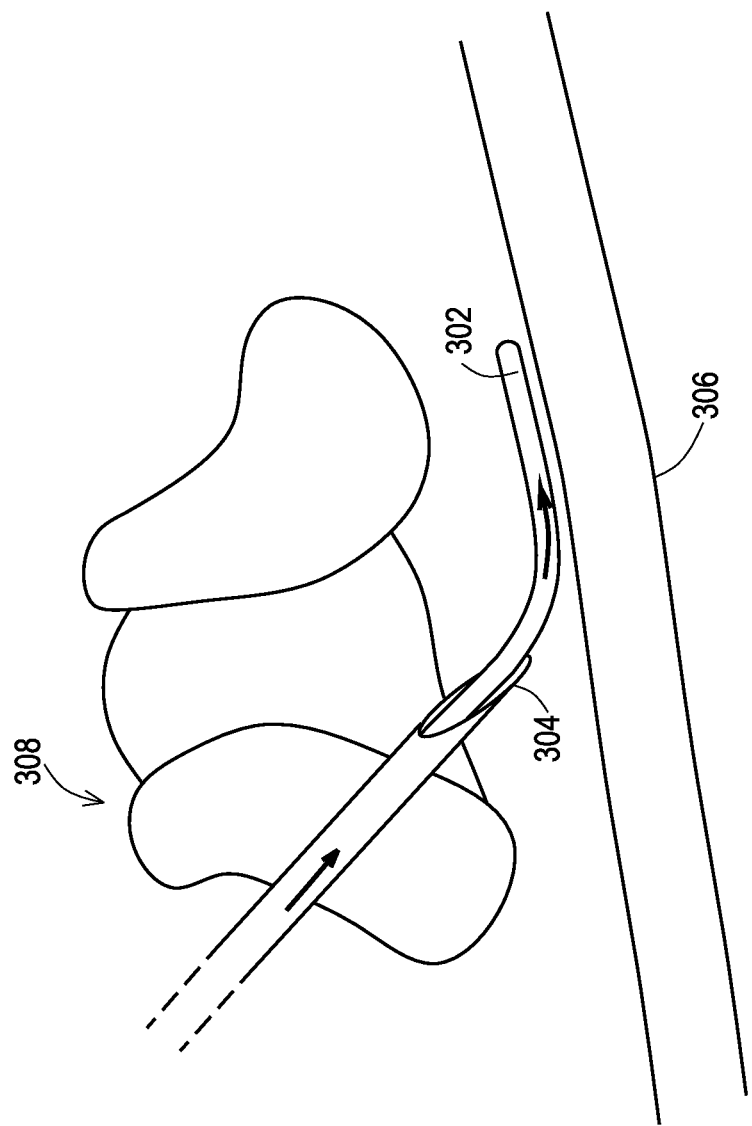
FIG. 3 shows an example of a procedure that begins with a needle being inserted into an epidural space followed by a guidewire.
Figure 11:
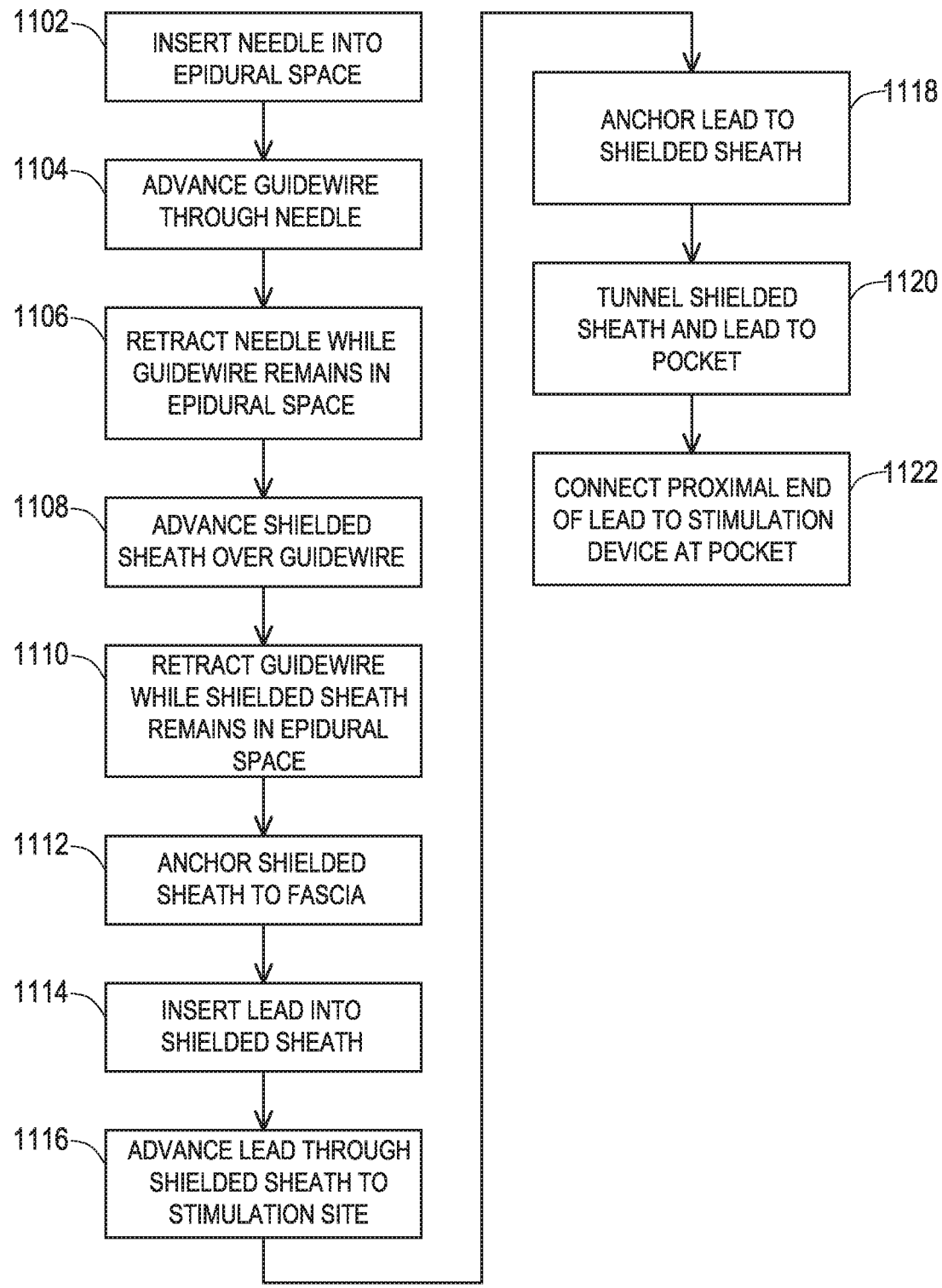
FIG. 11 shows a set of operations to implant a shielded sheath and an implantable medical lead according to the aspects shown in FIGS. 3-10.

In FIG. 11, the procedure for a new implantation of a lead 104 begins at an operation 1102 where a needle 304 as shown in FIG. 3 is being inserted through the spinal structures 308 and into the epidural space between the spinal structures 308 and the spinal cord 306. A guide wire 302 is then advanced through the needle 304 and into the epidural space at an operation 1104.

Figure 4:
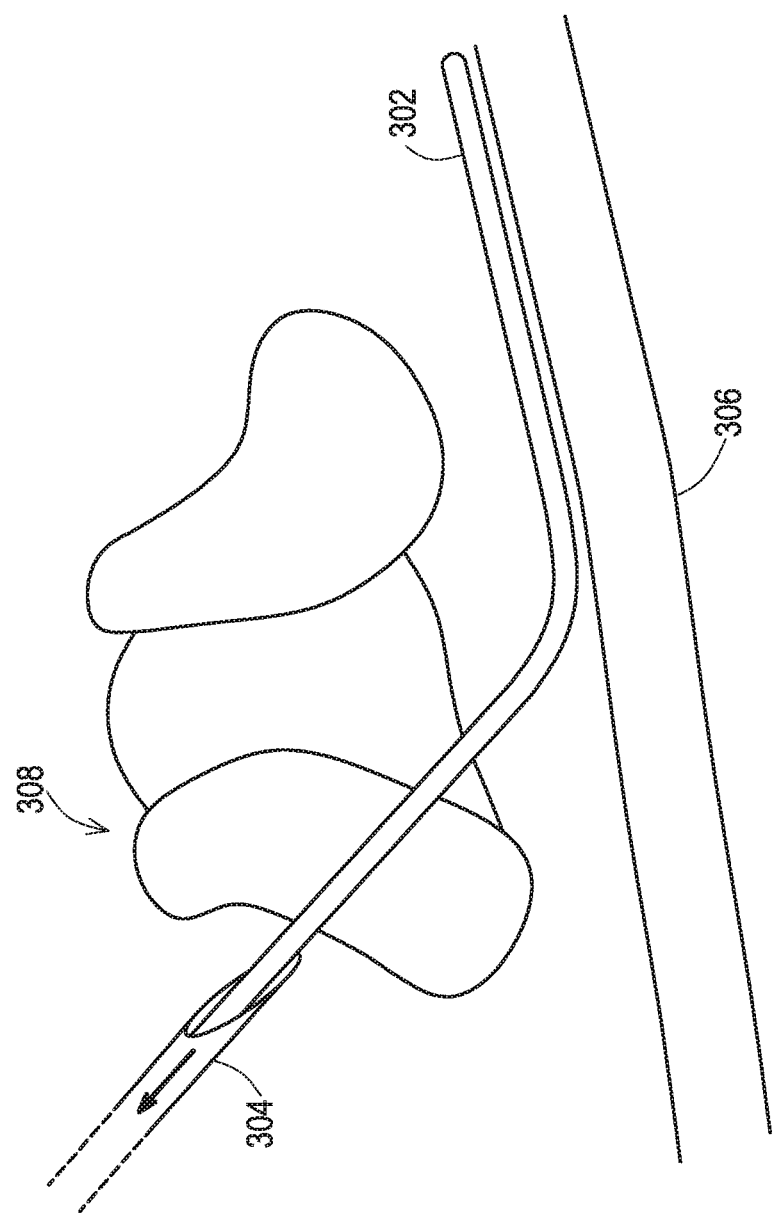
FIG. 4 shows the needle being removed from the epidural space while the guidewire remains.

At an operation 1106, the needle 304 is then retracted while the guidewire 302 remains in the epidural space. This is shown in FIG. 4 where it can be seen that the guidewire 302 has maintained a position within the epidural space as the needle 304 has exited the epidural space.

Figure 5:
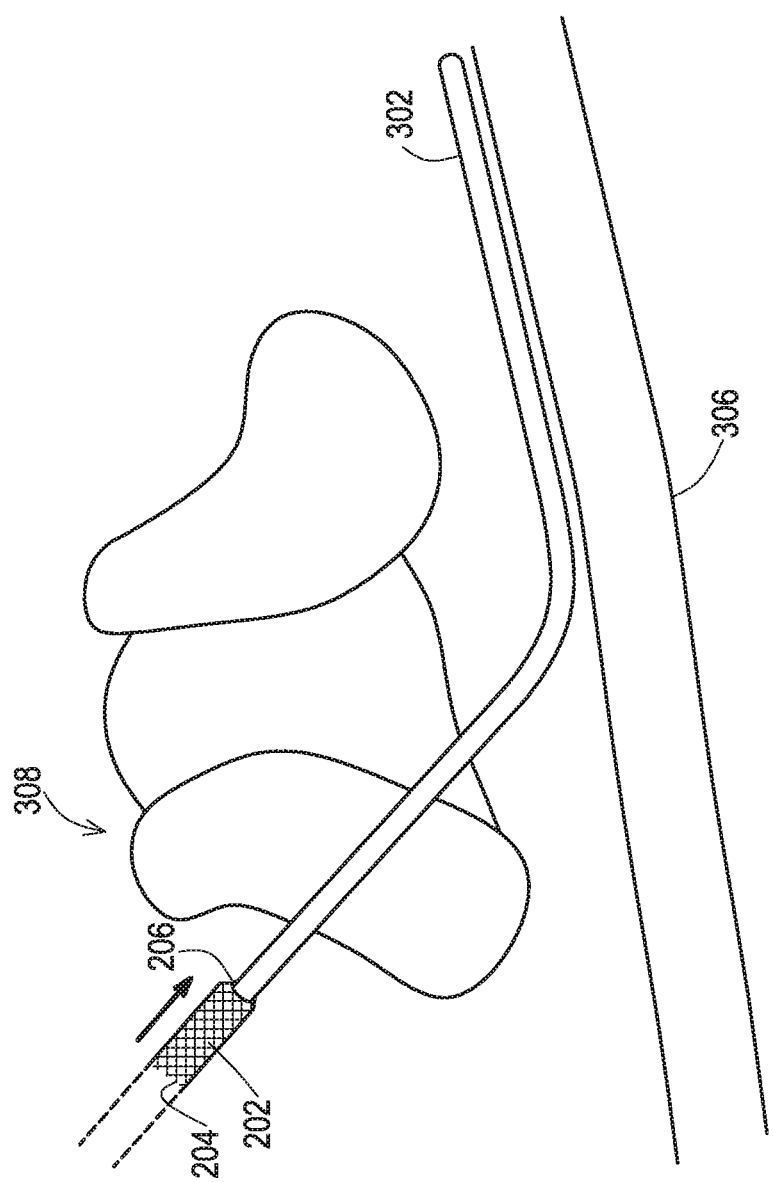
FIG. 5 shows an example of the shielded sheath being inserted into the epidural space by following along the guidewire.

At an operation 1108, the shielded sheath 202 having the shield layer 204 is advanced over the guidewire 302 and approaches the epidural space through the spinal structures 308. This is shown in FIG. 5. In this example, the shielded sheath 202 includes a tapered leading edge 206 which allows the shielded sheath 202 to more easily penetrate through the body tissues to reach the epidural space.

Figure 6:
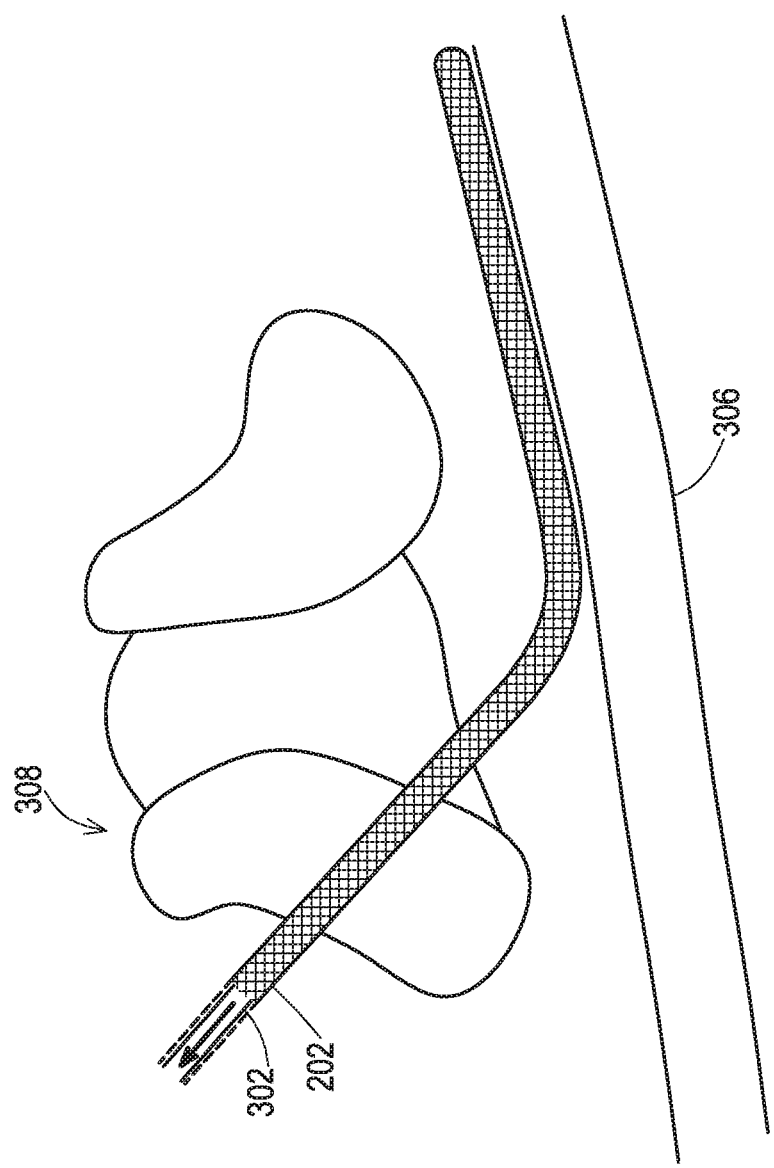
FIG. 6 shows removal of the guidewire from the epidural space while the shielded sheath remains.

At an operation 1110, the guidewire 302 is retracted from the epidural space through the shielded sheath 202 while the shielded sheath 202 remains in the epidural space. This is shown in FIG. 6 where it can be seen that the shielded sheath 202 has maintained a position within the epidural space as the guidewire 302 has exited the epidural space.

Figure 7:
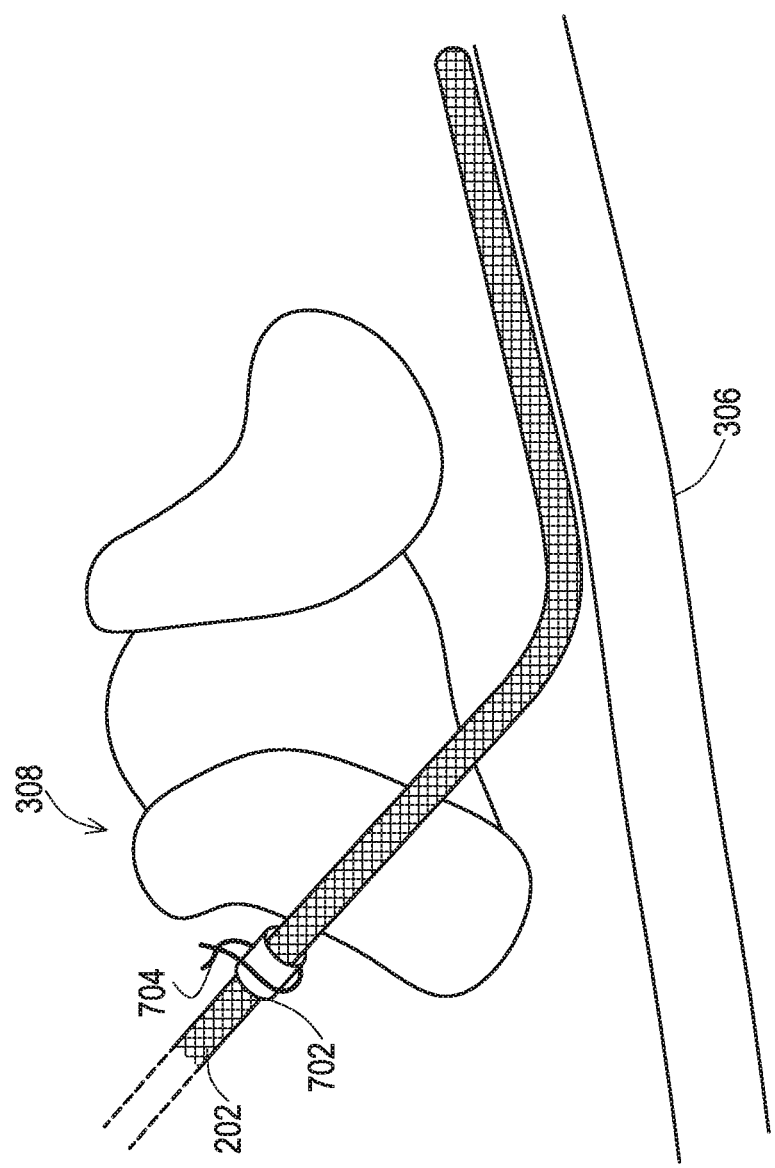
FIG. 7 shows an anchor being applied to hold the shielded sheath in place relative to the epidural space.

At an operation 1112, an anchor 702 as shown in FIG. 7 is applied to the shielded sheath 202 to fasten the shield to the surrounding fascia at the spinal structures 308. In the example shown in FIG. 7, the anchor 702 is of the type that forms a sleeve that is then affixed to surrounding tissue via sutures 704. However, other types of anchoring may also be used. For instance, the shielded sheath 202 may be directly sutured.

Figure 8:
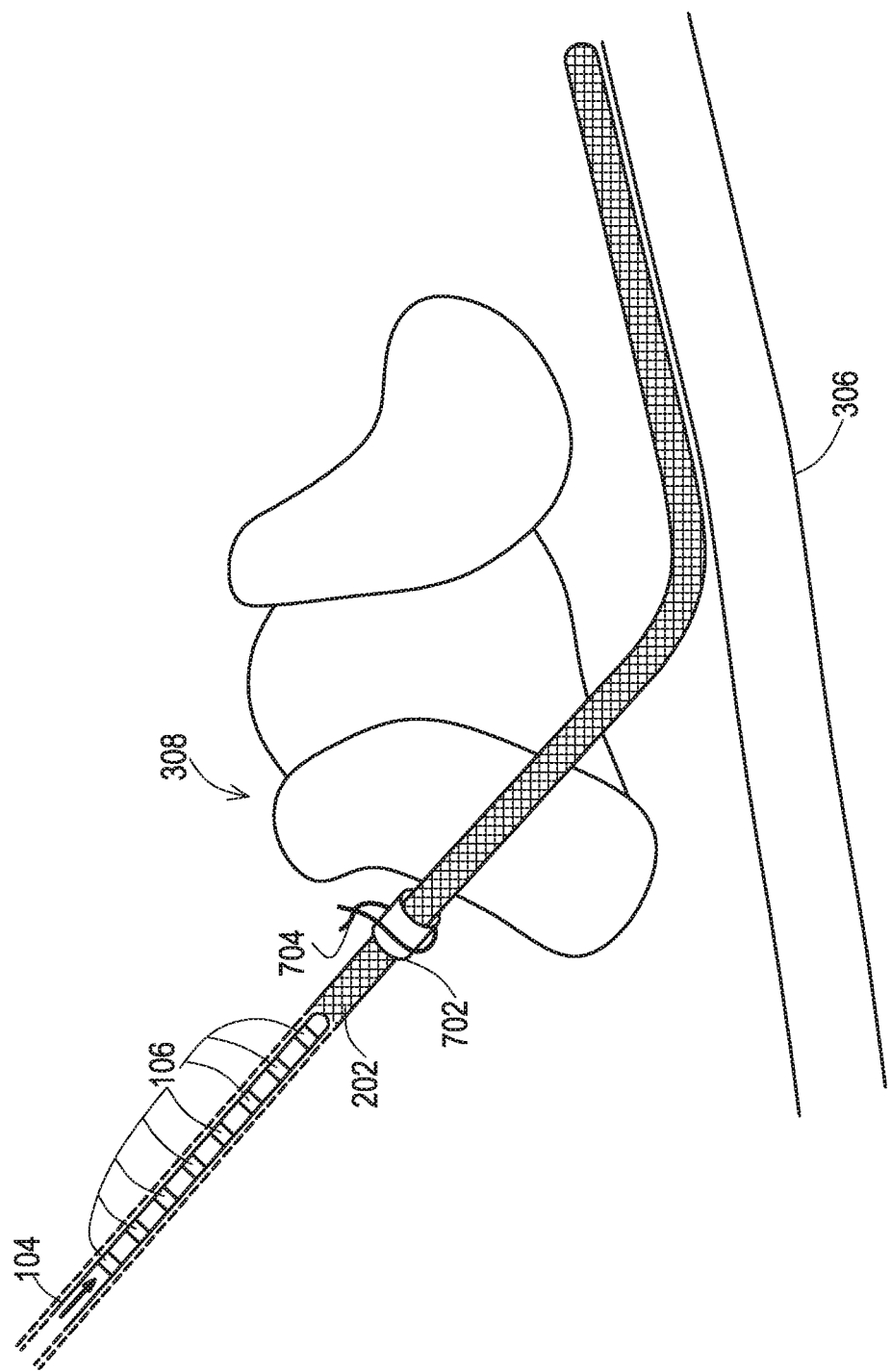
FIG. 8 shows an implantable medical lead being inserted into the epidural space by passing through the shield sheath.

At an operation 1114, the distal end of the lead 104 is inserted into the lumen of the shielded sheath 202 and is advanced toward the epidural space. This is shown in FIG. 8.

Figure 9:
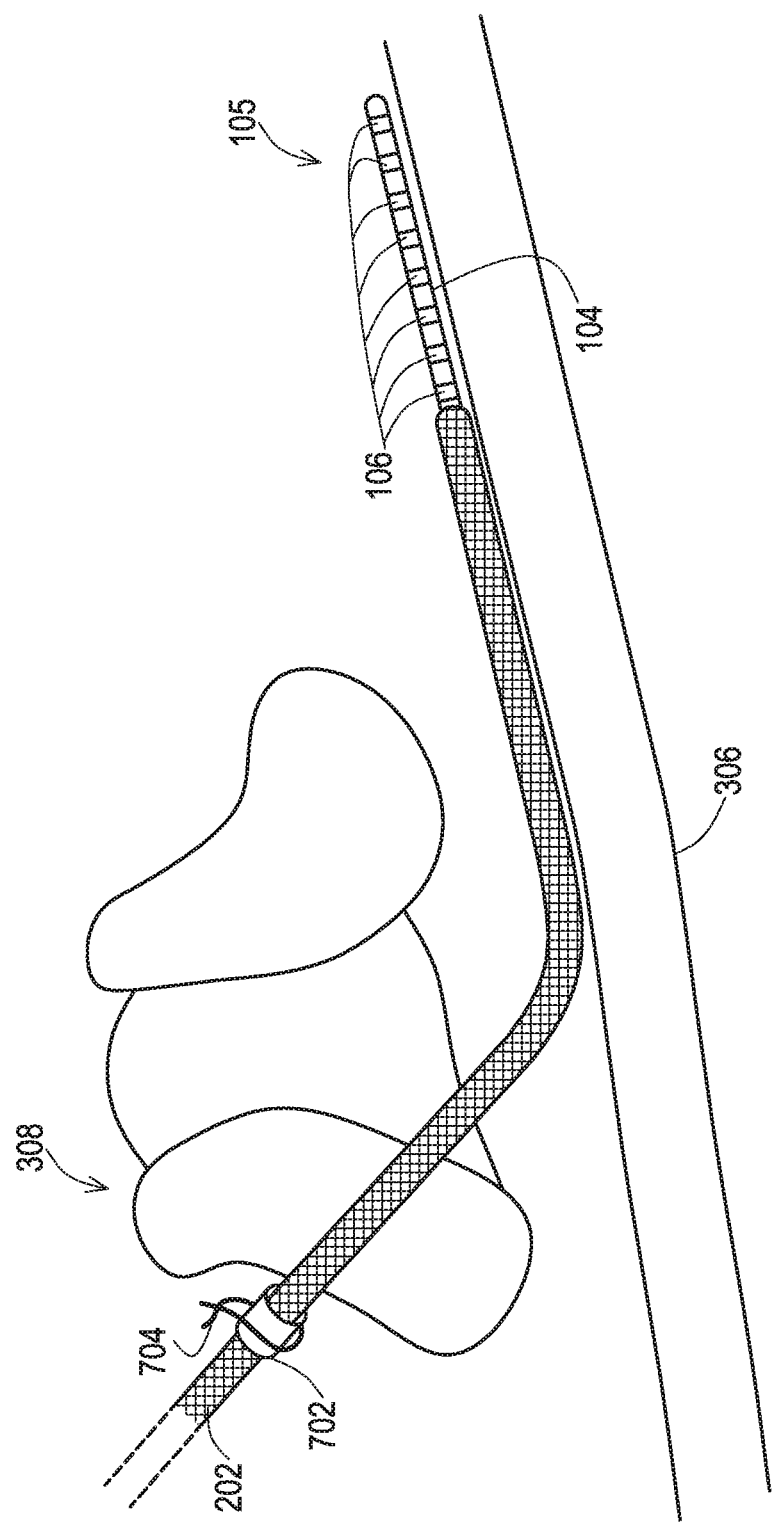
FIG. 9 shows distal end of the implantable medical lead exiting the distal end of the shielded sheath within the epidural space to reach the stimulation site.

At an operation 1116, the lead 104 is advanced through the shielded sheath 202 to the stimulation site. As shown in FIG. 9, the distal end 105 of the lead 104 exits from the shielded sheath to then reach the stimulation site within the epidural space with the electrodes 106 being exposed to the spinal cord 306.

Figure 10:
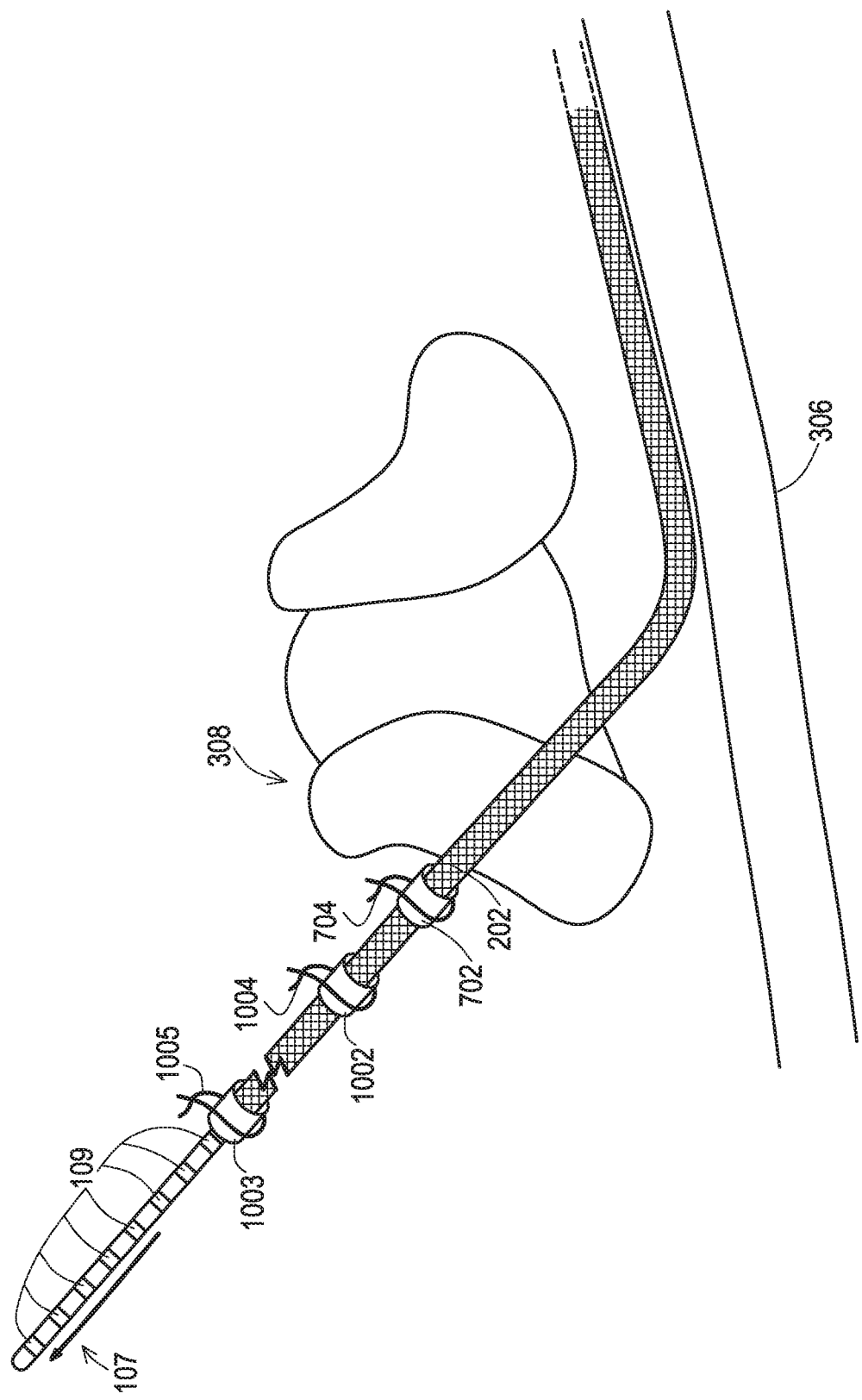
FIG. 10 shows an anchor being applied to hold the lead in place with the shielded sheath relative to the epidural space followed by the proximal end of the lead and shielded sheath being tunneled to the pocket for the implantable medical device.

At an operation 1118, an anchor 1002 as shown in FIG. 10 is applied to the shielded sheath 202 to further fasten the shield to the surrounding fascia at the spinal structures 308 while also anchoring the lead to the shielded sheath. This, in turn, anchors the lead to the surrounding fascia. In the example shown in FIG. 10, the anchor 1002 is also of the type that forms a sleeve that is then affixed to surrounding tissue via sutures 1004. In the example shown in FIG. 10, another anchor 1003 is also installed at the point where the lead 104 exits the proximal end of the shielded sheath and affixed to surrounding tissue via sutures 1005. By overlapping the point where the lead 104 exits the shielded sheath, this anchor 1003 is partially directly engaging the lead 104 and partially directly engaging the shielded sheath to further anchor the lead 104 and shielded sheath together and to the tissue. However, other types of anchoring may also be used for the purpose of anchoring the lead to the shielded sheath. For instance, the shielded sheath may be provided with elasticity of the insulative body and a slightly smaller lumen diameter than the lead 104 near the ends such that the compression of the shielded sheath may anchor the sheath to the lead 104. Other examples of anchoring include utilizing an anchor that is elastic and provides compression to force the sheath tightly against the lead.

At an operation 1120, the proximal end 107 of the lead 104 having proximal contacts 109 and the shielded sheath 202 are tunneled together to the pocket 114 where the implantable medical device 102 is or will be positioned. This is also shown in FIG. 10.

At an operation 1122, the proximal end 107 of the lead 104 is connected to the implantable medical device 102 at the pocket 114. The proximal contacts 109 of the lead 104 establish electrical connections with corresponding electrical connectors of the implantable medical device 102 to complete the stimulation pathway to the electrodes 106 that are positioned at the stimulation site within the epidural space.

Figure 17:
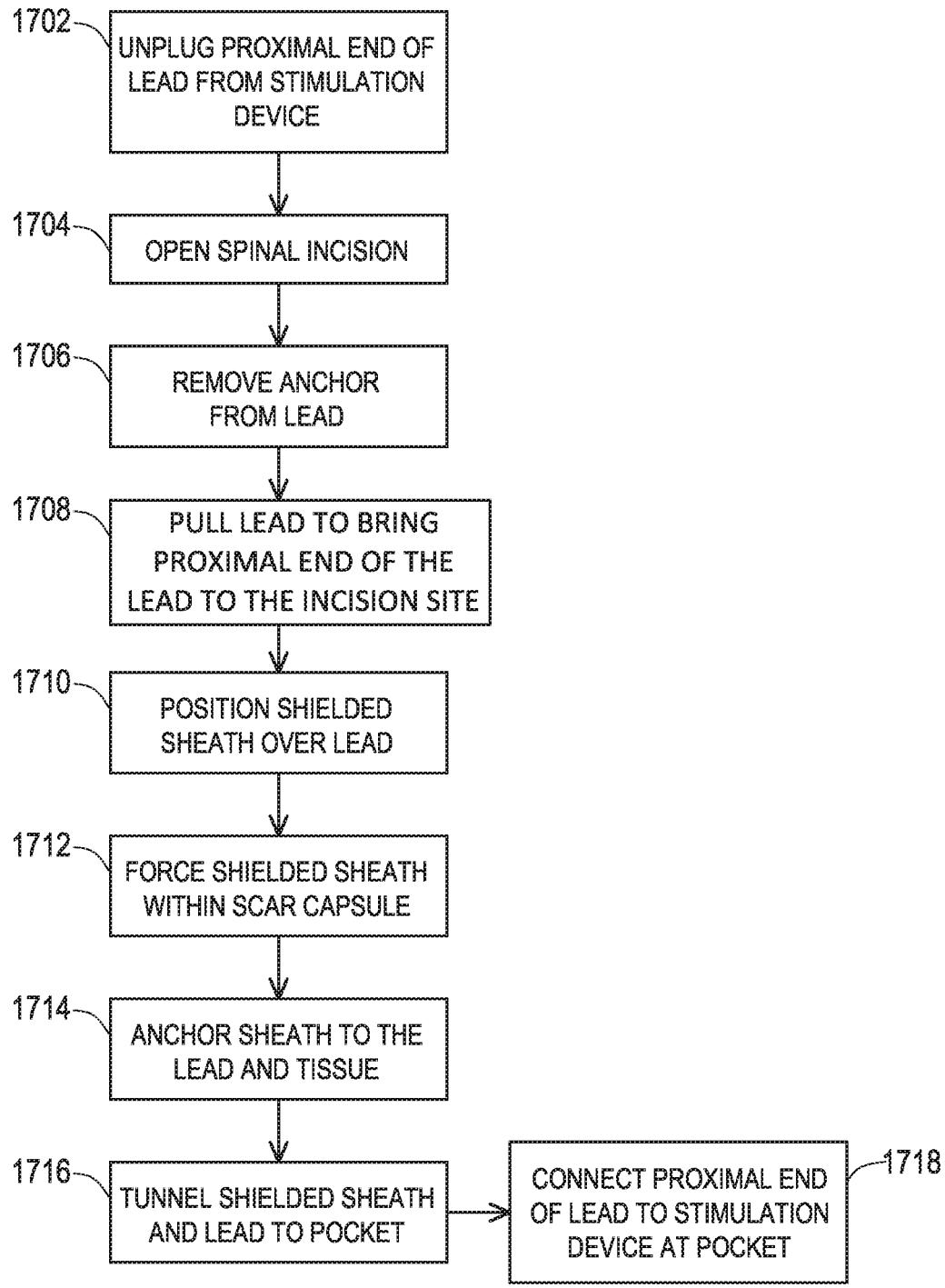
FIG. 17 shows a set of operations to add a shielded sheath over an implanted lead according to the aspects shown in FIGS. 12-16.

In FIG. 17, the procedure for a previously implanted lead 104 begins at an operation 1702 where the proximal end of the lead 107 is unplugged from the implantable medical device 102. A spinal incision is then opened nearby the entry site to the epidural space at an operation 1704.

Figure 12:
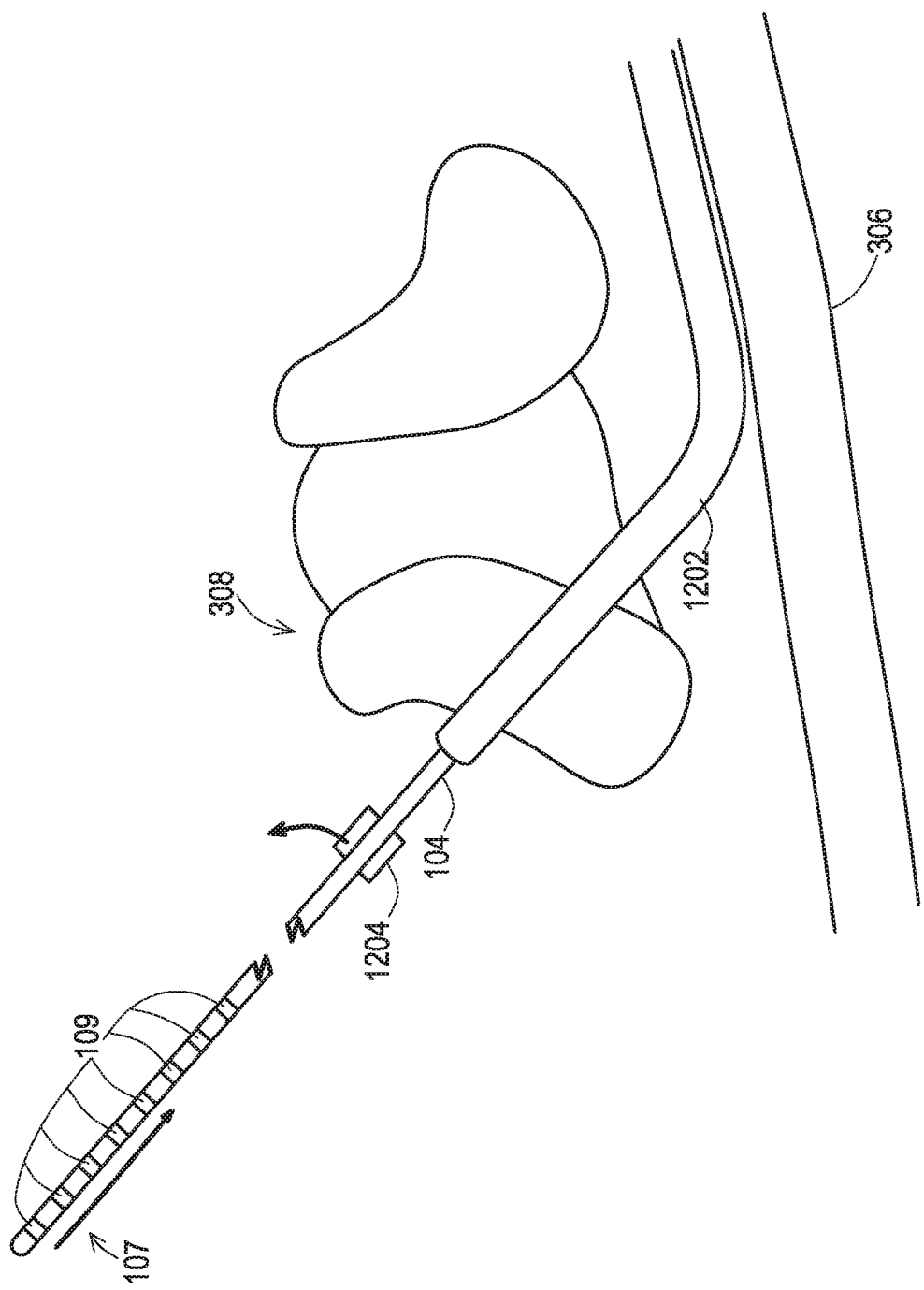
FIG. 12 shows an example of a procedure that begins with an anchor being removed from a lead that is implanted with a distal end in the epidural space and a proximal end of the lead being pulled to the incision site for entry to the epidural space.

At an operation 1706, an anchor 1204 as shown in FIG. 12 is being removed from the lead 104. Then, at an operation 1708, the lead 104 is pulled at the incision site to bring the proximal end 107 of the lead 104 to the incision cite. This is also shown in FIG. 12. It can further be seen in FIG. 12 that the distal end of the lead 104 is present within a scar capsule 1202 that has naturally formed about the distal end of the lead 104.

Figure 13:
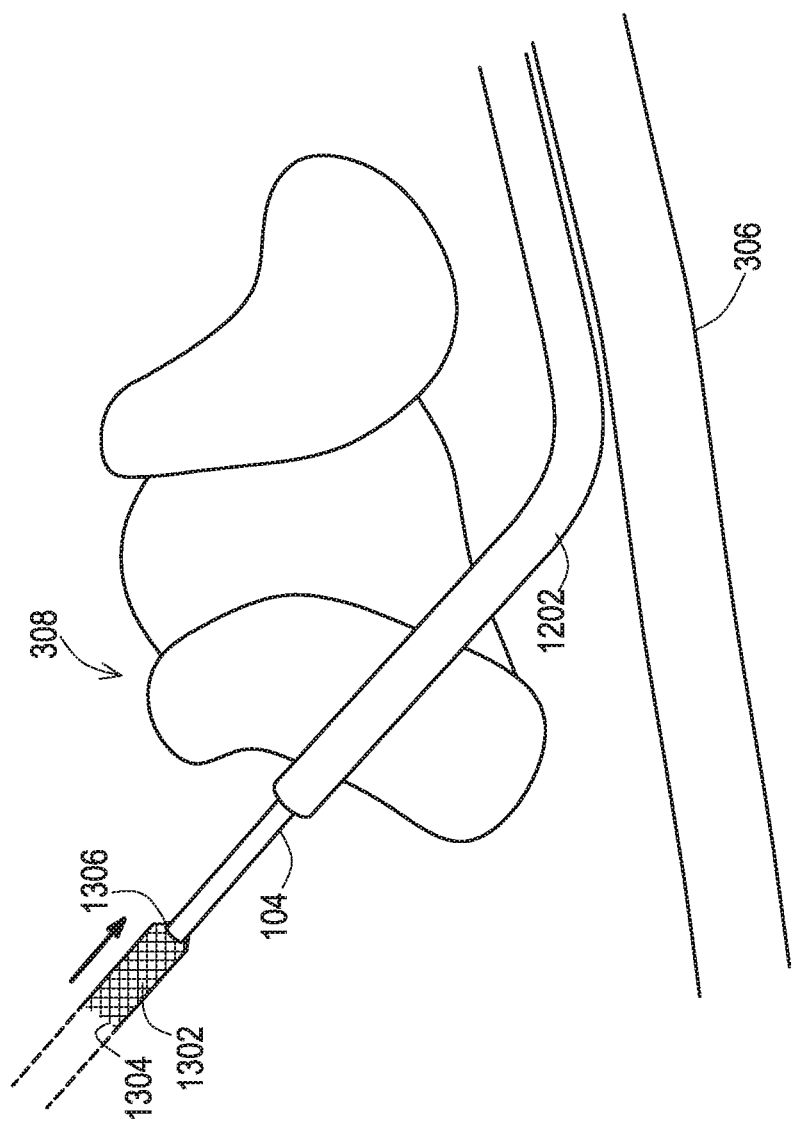
FIG. 13 shows an example of the shielded sheath being inserted over the implanted lead.

At an operation 1710, a shielded sheath 1302 is positioned over the lead 104 with the proximal end 107 of the lead 104 entering the lumen of the shielded sheath 202. This is shown in FIG. 13. The shielded sheath 1302 may be the same or different construction as the shielded sheath 202 and includes a shield layer 1304 that may be the same or different construction as the shield layer 204.

Figure 14:
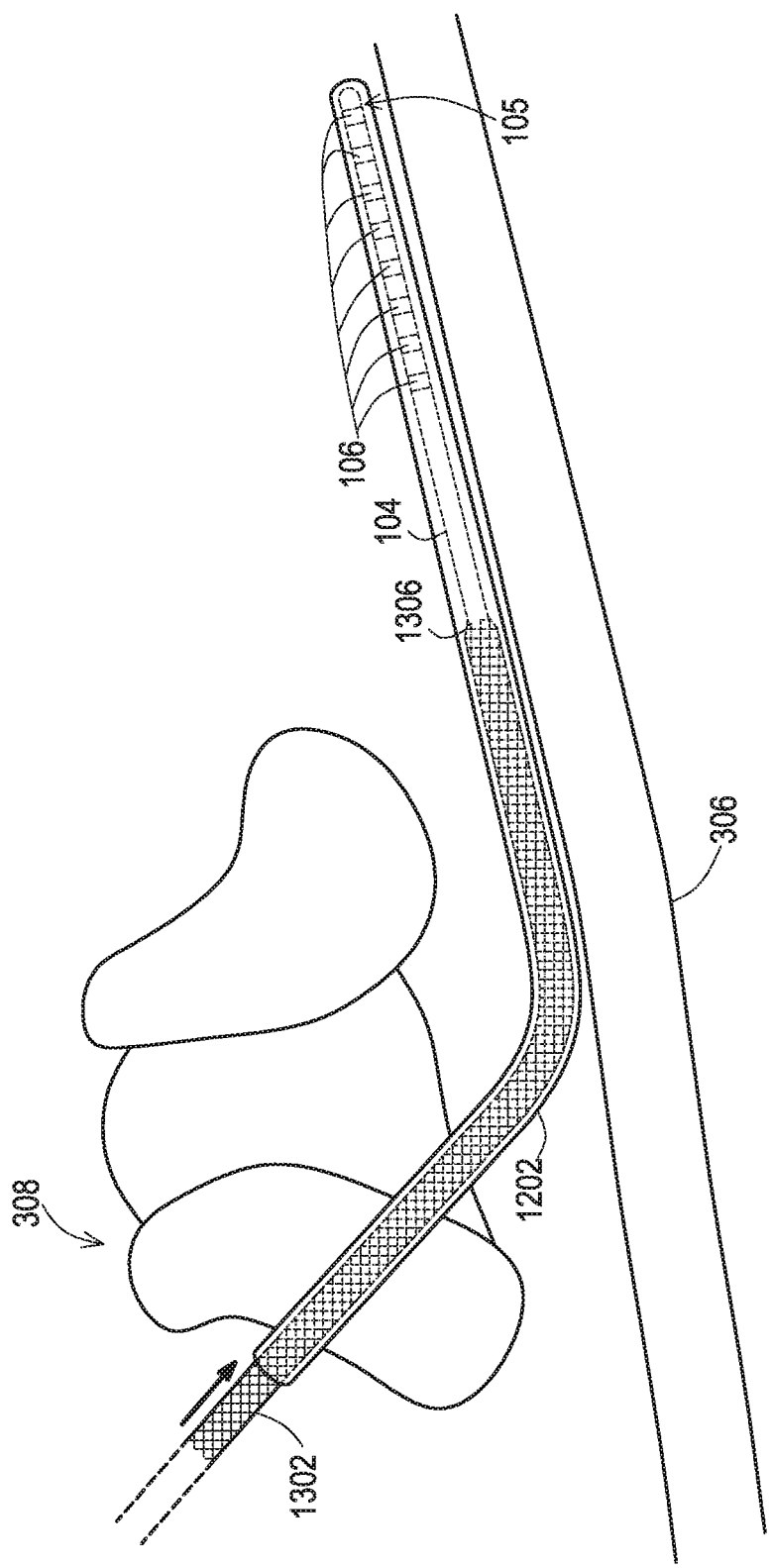
FIG. 14 shows the shield sheath passing through a scar capsule that surrounds the implanted lead and passing into the epidural space.

At an operation 1712, the shielded sheath 1302 is forced within the scar capsule 1202. A tapered leading edge 1306 may be included on the shielded sheath 1302 to assist in penetrating into the scar capsule 1202. This is shown in FIG. 14. The shielded sheath is advanced through the scar capsule 1202 until reaching a desired position proximal of the electrodes 106 on the distal end 105 of the lead 104 as shown in FIG. 15.

Figure 15:
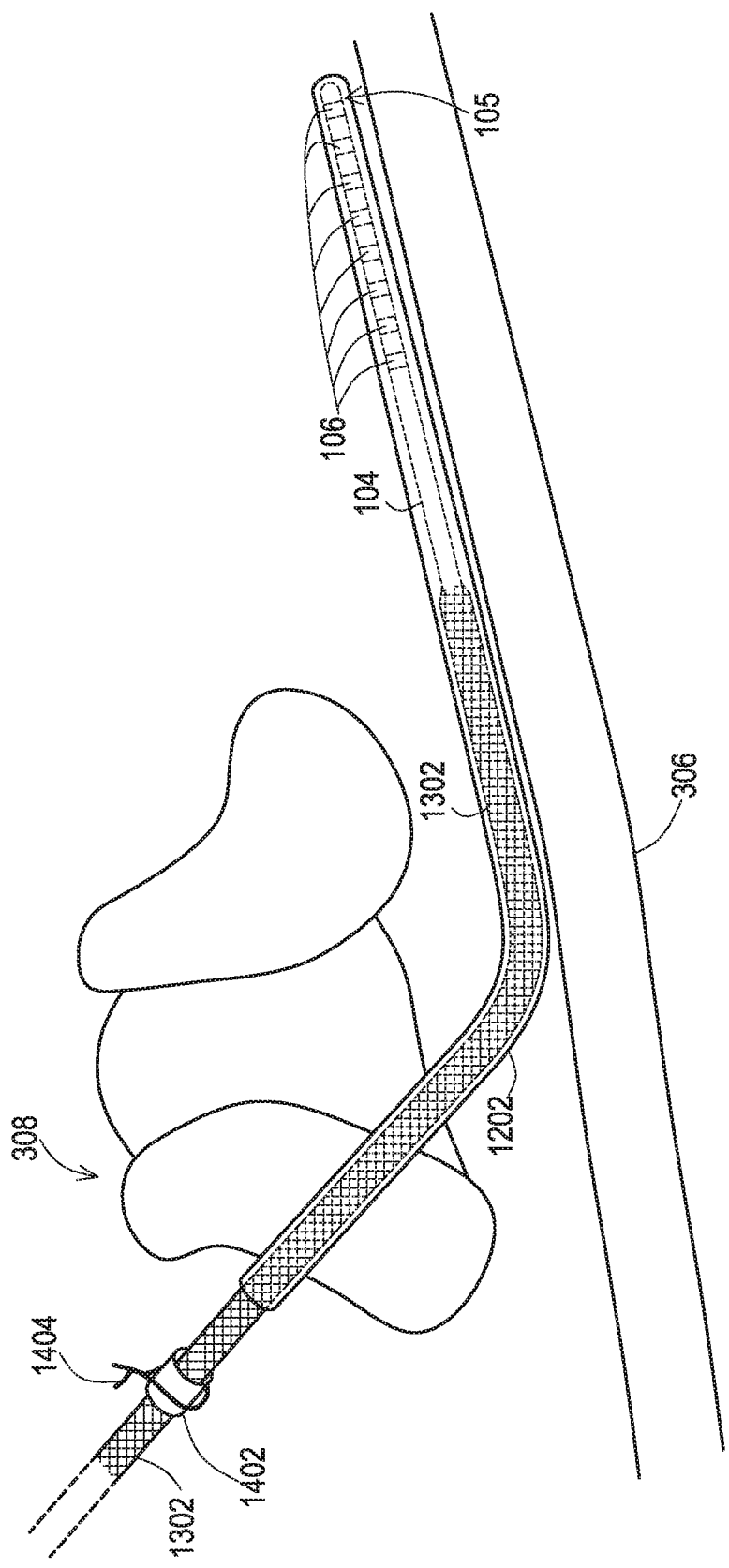
FIG. 15 shows an anchor being applied to hold the shielded sheath and lead in place relative to the epidural space.

At an operation 1714, an anchor 1402 as also shown in FIG. 15 is applied to the shielded sheath 1302 to fasten the shielded sheath 1302 to the surrounding fascia at the spinal structures 308 while also anchoring the lead 104 to the shielded sheath 1302. This, in turn, anchors the lead 104 to the surrounding fascia. In the example shown in FIG. 15, the anchor 1402 is also of the type that forms a sleeve that is then affixed to surrounding tissue via sutures 1404. However, other types of anchoring may also be used for the purpose of anchoring the lead to the shielded sheath. For instance, the shielded sheath may be provided with elasticity of the insulative body and a slightly smaller lumen diameter than the lead 104 near the ends such that the compression of the shielded sheath may anchor the sheath to the lead 104. Other examples of anchoring include utilizing an anchor that is elastic and provides compression to force the sheath tightly against the lead.

Figure 16:
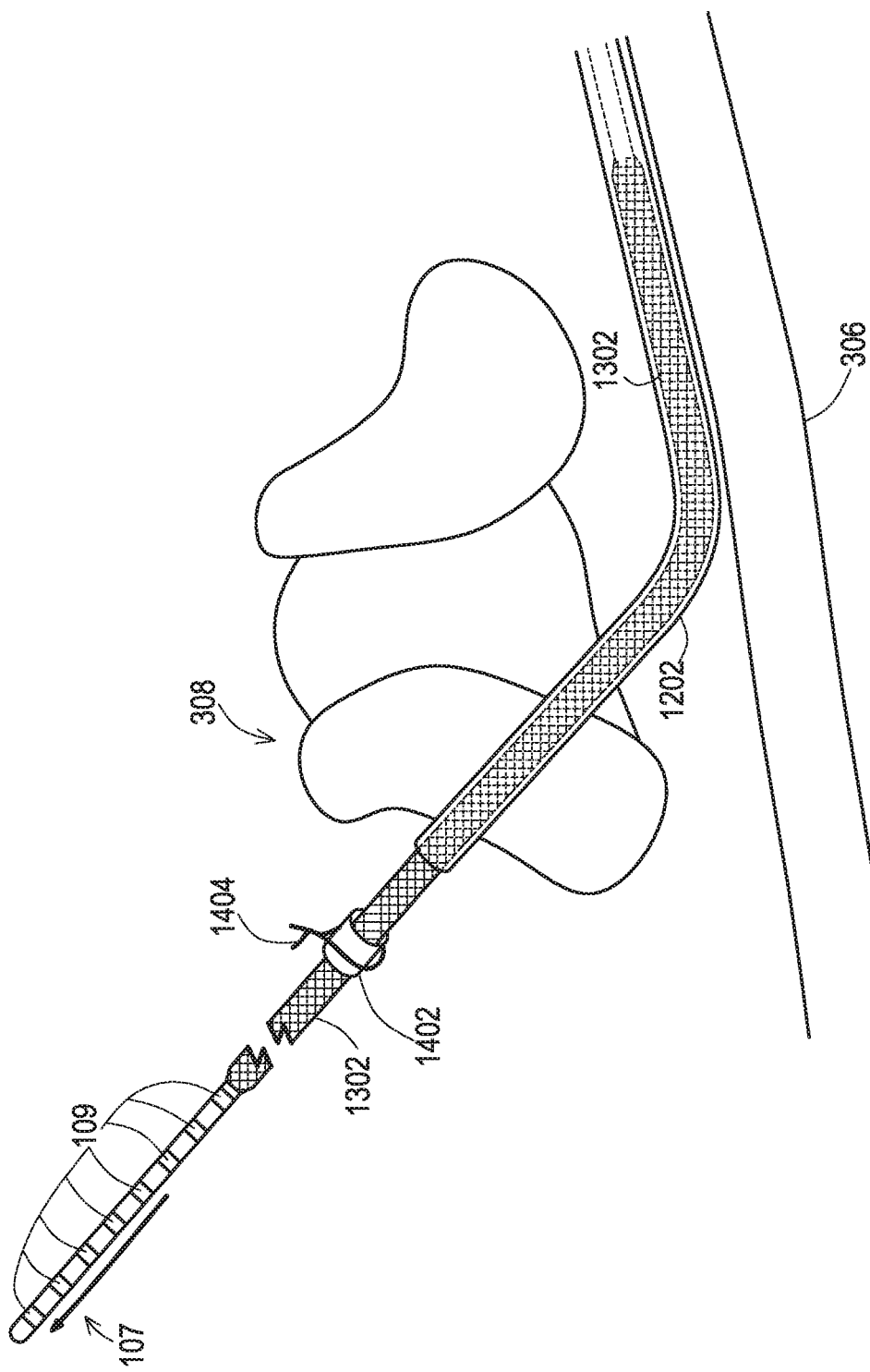
FIG. 16 shows the proximal end of the lead and shielded sheath being tunneled to the pocket for the implantable medical device.

At an operation 1716, the proximal end 107 of the lead 104 having proximal contacts 109 and the shielded sheath 1302 are tunneled together to the pocket 114 where the implantable medical device 102 is or will be positioned. This is shown in FIG. 16.

At an operation 1718, the proximal end 107 of the lead 104 is connected to the implantable medical device 102 at the pocket 114. The proximal contacts 109 of the lead 104 establish electrical connections with corresponding electrical connectors of the implantable medical device 102 to complete the stimulation pathway to the electrodes 106 that are positioned at the stimulation site within the epidural space.

Figure 18:
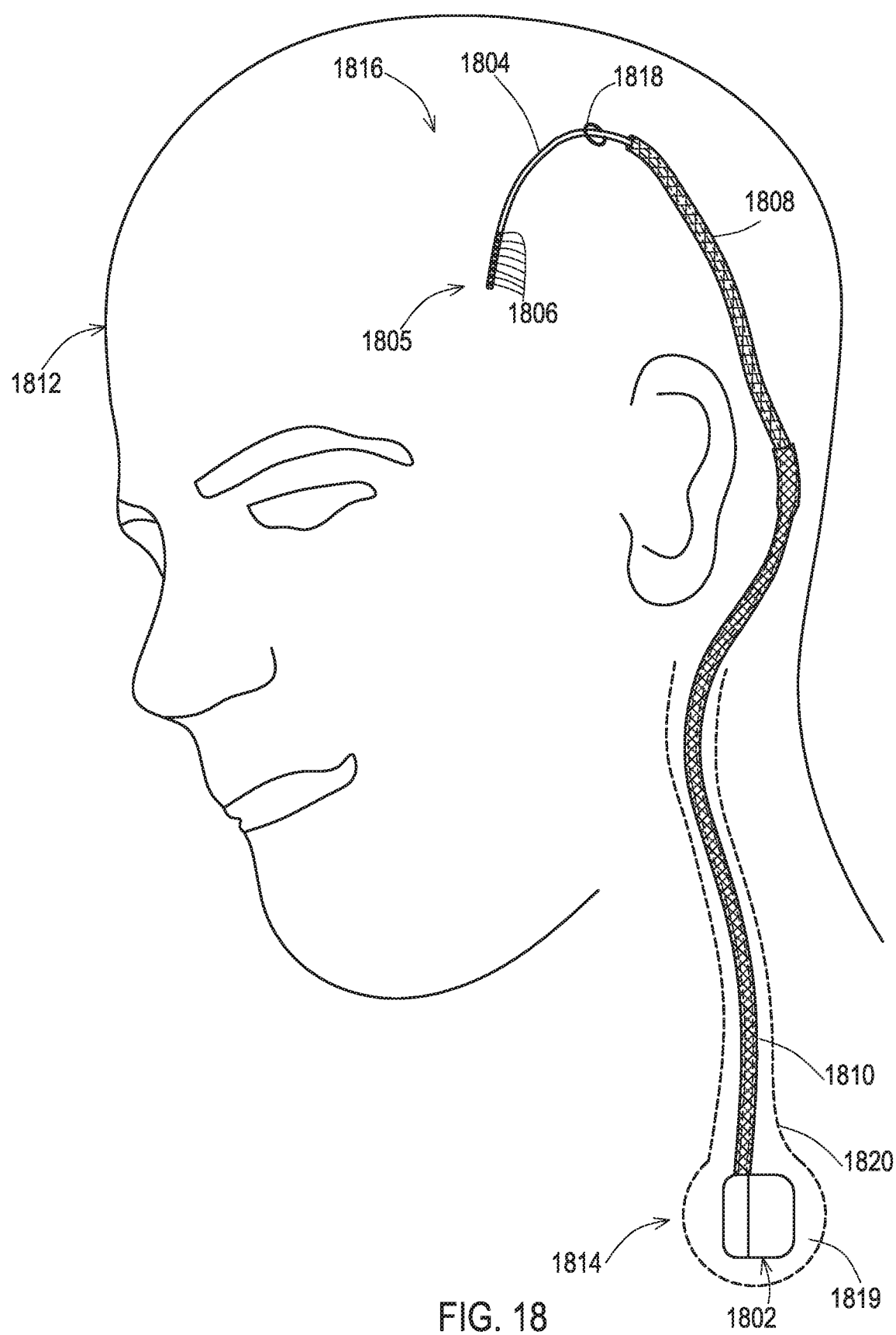
FIG. 18 shows another example of an implantable medical system including a lead extension with shielded sheaths installed over a lead and a lead extension.

FIG. 18 shows an implantable medical system 1814 which includes an implantable medical device 1802, an implantable medical lead 1804, and a lead extension that is connected between the lead 1804 and the implantable medical device 1802. The implantable medical device 1802 is positioned within a pocket 1819 formed in the upper torso and the lead extension extends through a subcutaneous tunnel 1820 formed when implanting the extension. The proximal end 1805 of the lead 1804 passes through the cranium via a hole 1818 to reach a stimulation site within the brain 1816 of the patient 1812.

The system 1814 also includes a first shielded sheath 1808 that has been placed over the lead 1804 and a second shielded sheath 1810 that has been placed over the lead extension. The shielded sheath 1808 is positioned between the proximal end where the lead 1804 connects to the extension and the distal end 1805 where the electrodes 1806 are located. The shielded sheath 1810 is positioned between the proximal end where the extension connects to the implantable medical device and the distal end where a connector housing is located. The shielded sheaths may be constructed like the examples discussed above for shielded sheath 202 and 2600. A cranial anchor may be installed onto the lead 1804 at the hole 1818 and the sheath 1808 naturally maintains its position between the hole 1818 and the distal connector 2102 of the extension 2104. Likewise, the second sheath 1810 naturally maintains its position between the distal end of the distal connector 2102 and the proximal end of the extension 2104. However, if desired, anchoring may be provided on the sheath 1808 and second sheath 1810 in this instance as well in the same manners as discussed above with respect to the spinal implantations.

Figure 19:
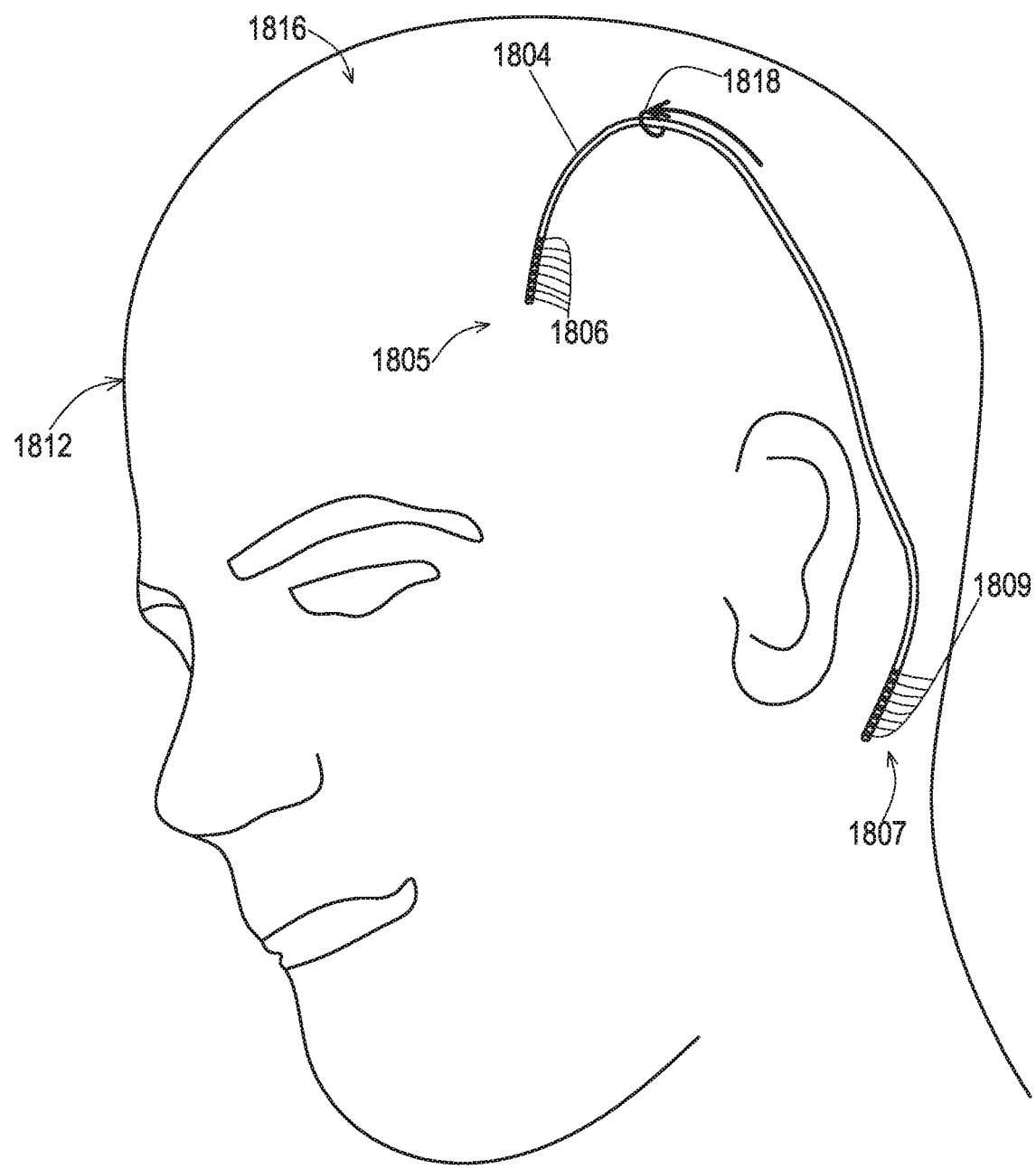
FIG. 19 shows an example of a procedure that begins with a lead being tunneled to a bore hole with a distal end of the lead being inserted into the brain to a stimulation site.
Figure 23:
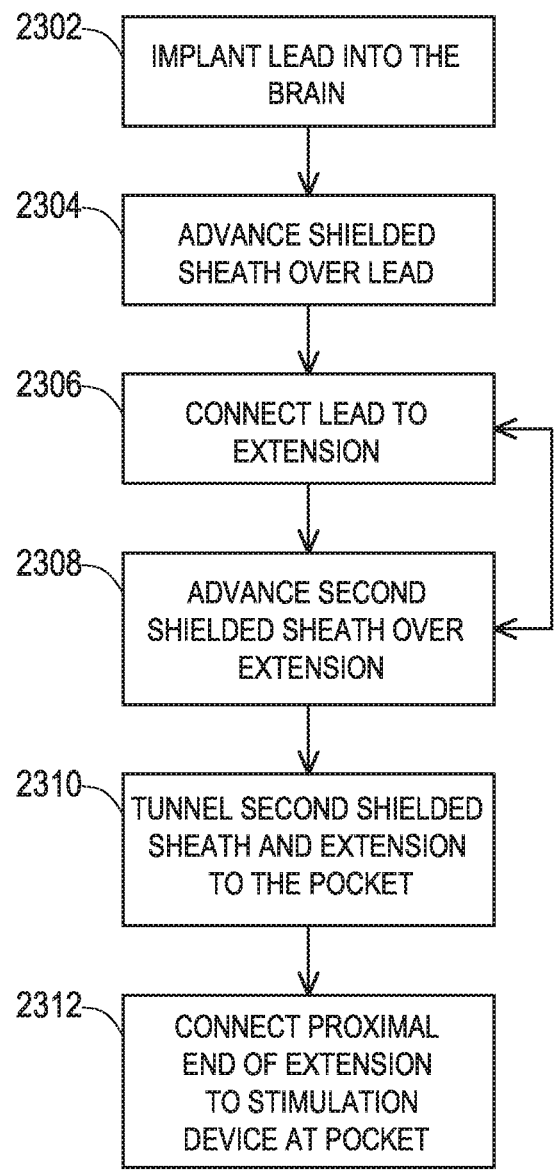
FIG. 23 shows a set of operations to add a shielded sheath over the implanted lead and to add a second shielded sheath over the implanted extension according to the aspects shown in FIGS. 19-22.

In FIG. 23, the procedure for implanting the lead 1804, extension, and shielded sheaths 1808, 1810 begins at an operation 2302 where the lead 1804 as shown in FIG. 19 is being inserted through the hole 1818 of the cranium and into the brain 1816. The lead 1804 may be routed subcutaneously from an area behind the ear of the patient up to the hole 1818. The lead 104 may be anchored nearby the hole 1818.

Figure 20:
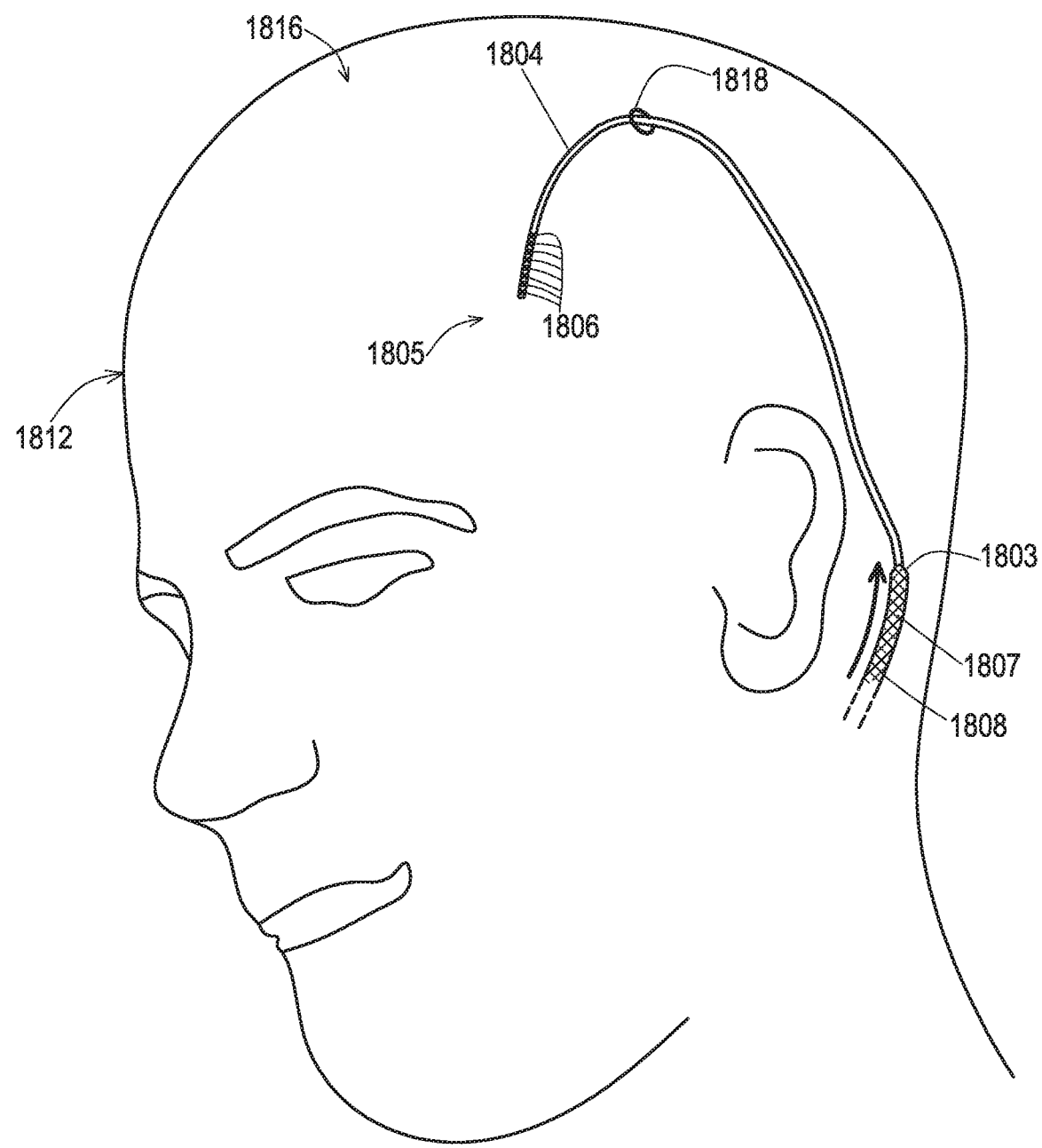
FIG. 20 shows an example of a shielded sheath being inserted over the lead.

In an operation 2304, the first shielded sheath 1808 is advanced over the lead 104. The proximal end of the lead 104 is inserted into the lumen of the shielded sheath 1808 and the shielded sheath 1808 is advanced toward the hole 1818. This is shown in FIG. 20. It can be seen that the shielded sheath 1808 has a tapered leading edge 1803 that assists in passing subcutaneously toward the hole 1818. It can also be seen that the shielded sheath 1808 has a shield layer 1807.

Figure 21:
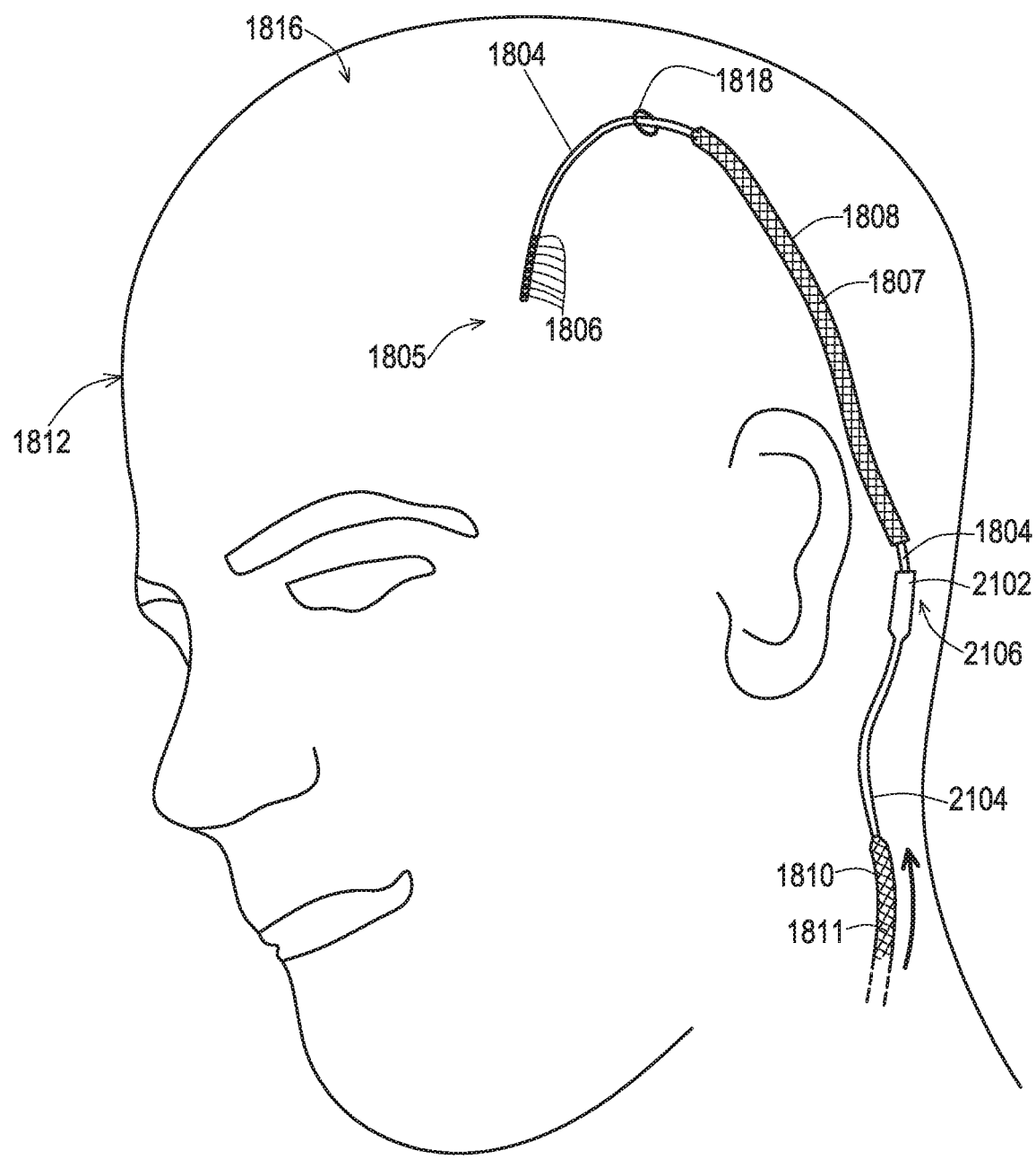
FIG. 21 shows an example of a second shielded sheath being inserted over a lead extension that has been tunneled and connected to a proximal end of the lead.

In an operation 2306, the proximal end of the lead 1804 is connected to the distal end connector 2102 on a distal end 2106 of the lead extension 2104 as shown in FIG. 21. This occurs via an incision site that has been created when initially tunneling the lead to the hole 1818. As also shown in FIG. 21, the second shielded sheath 1810 having a shield layer 1811 is advanced over the lead extension 2104 at an operation 2308.

Figure 22:
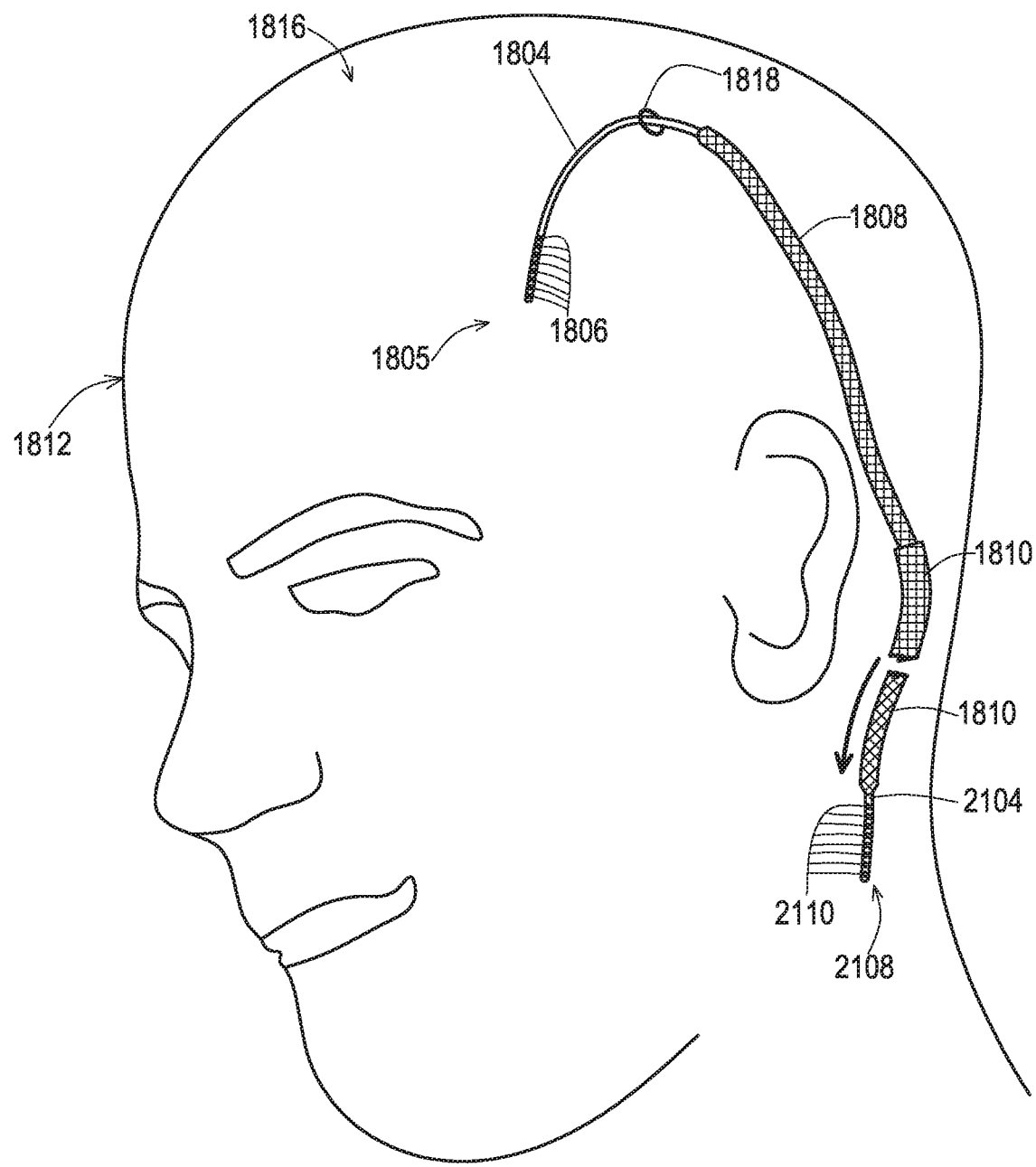
FIG. 22 shows the proximal end of the extension and the second shielded sheath being tunneled to the pocket for the implantable medical device.

In an operation 2308, the proximal end 2108 of the extension 2104 having proximal contacts 2110 and the second shielded sheath 1810 are tunneled together to the pocket 1819 where the implantable medical device 1802 is or will be positioned. This is shown in FIG. 22.

At an operation 2312, the proximal end 2108 of the extension 2104 is connected to the implantable medical device 1802 at the pocket 1819. The proximal contacts 2110 of the extension 2104 establish electrical connections with corresponding electrical connectors of the implantable medical device 1802 to complete the stimulation pathway to the electrodes 1806 that are positioned at the stimulation site within the brain 1816.

Figure 24:
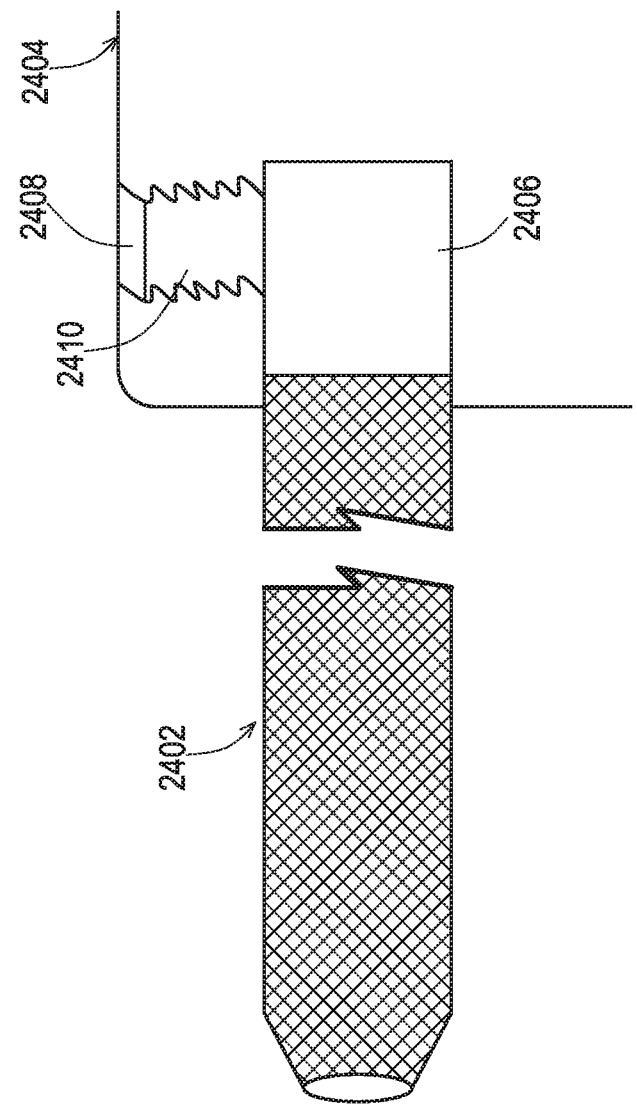
FIG. 24 shows a proximal end of an example of a shielded sheath that may include a connector for engagement with a contact of an implantable medical device.

FIG. 24 shows an example of a shielded sheath 2402 that may be placed over a lead or an extension where the proximal end of the shielded sheath 2402 provides connectivity. In this example, a proximal contact 2406 such as a metal ring is positioned on the proximal end. This proximal contact 2406 may be in physical contact with the shield layer of the shielded sheath 2402 to provide an electrical connection from the shield layer to the proximal contact 2406. An implantable medical device 2404 may receive the proximal end of the shielded sheath 2402 into a bore where the lead or lead extension may also be inserted.

The implantable medical device 2404 may include an electrical connector such as a set screw 2410 and a corresponding set screw bore 2408 that allows a physical connection to be made with the proximal contact. This electrical connector 2410 then provides an electrical pathway to a grounding surface at the implantable medical device such as a metal housing. This effectively provides a tissue ground at the implantable medical device 2404 for the shield layer of the shielded sheath 2402 such that RF energy coupled to the shield may be diverted to the grounding surface and surrounding tissue of the implantable medical device 2404.

Figure 25:
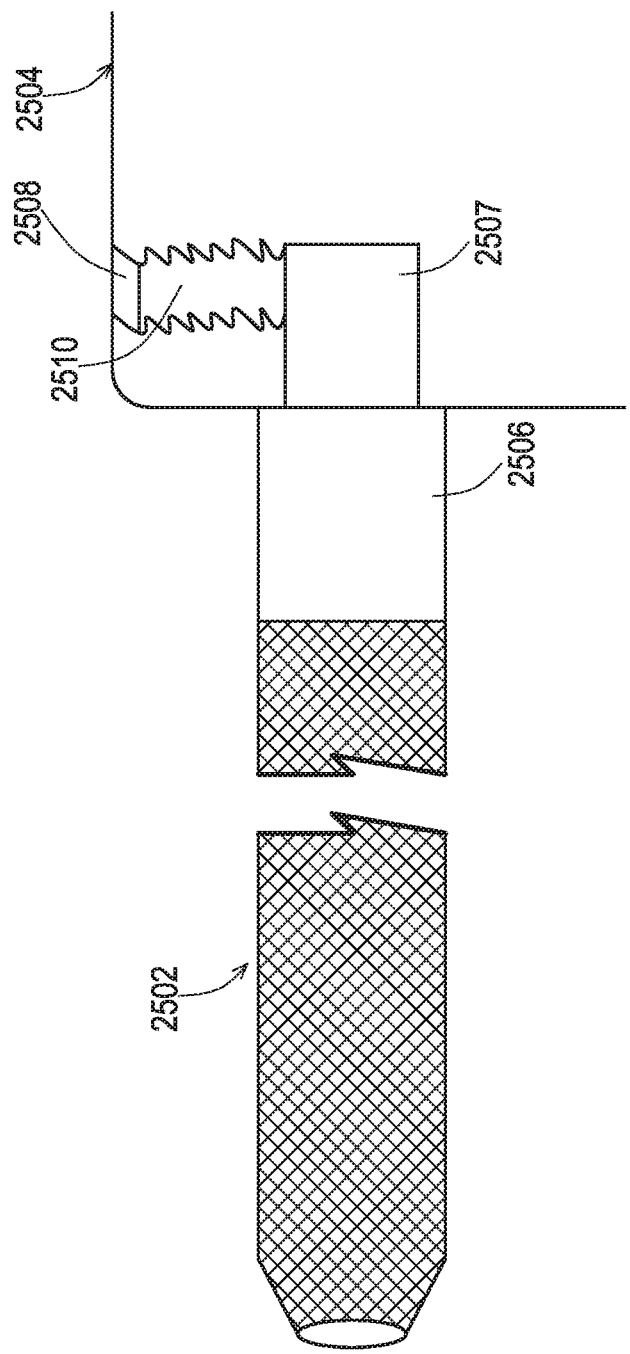
FIG. 25 shows a proximal end of another example of a shielded sheath that may include a connector with a reduced diameter portion for engagement with a contact of an implantable medical device.

FIG. 25 shows an example of a shielded sheath 2502 that may be placed over a lead or an extension where the proximal end of the shielded sheath 2502 also provides connectivity. In this example, a proximal contact 2506 such as a metal ring is positioned on the proximal end. This proximal contact 2506 may be in physical contact with the shield layer of the shielded sheath 2502 to provide an electrical connection from the shield layer to the proximal contact 2506. The proximal contact 2506 also includes a smaller diameter region 2507. An implantable medical device 2504 may receive the proximal end of the shielded sheath 2502 and specifically the smaller diameter region 2507 of the proximal contact 2506 into a bore where the lead or lead extension may also be inserted. This bore may have a diameter that is smaller than the larger diameter region of the proximal contact 2506 but large enough to accept the smaller diameter region 2507.

The implantable medical device 2504 may include an electrical connector such as a set screw 2510 and a corresponding set screw bore 2508 that allows a physical connection to be made with the proximal contact region 2507. This electrical connector 2510 then provides an electrical pathway to a grounding surface at the implantable medical device such as a metal housing. This example also effectively provides a tissue ground at the implantable medical device 2504 for the shield layer of the shielded sheath 2502 such that RF energy coupled to the shield may be diverted to the grounding surface and surrounding tissue of the implantable medical device 2504.

Figure 27:
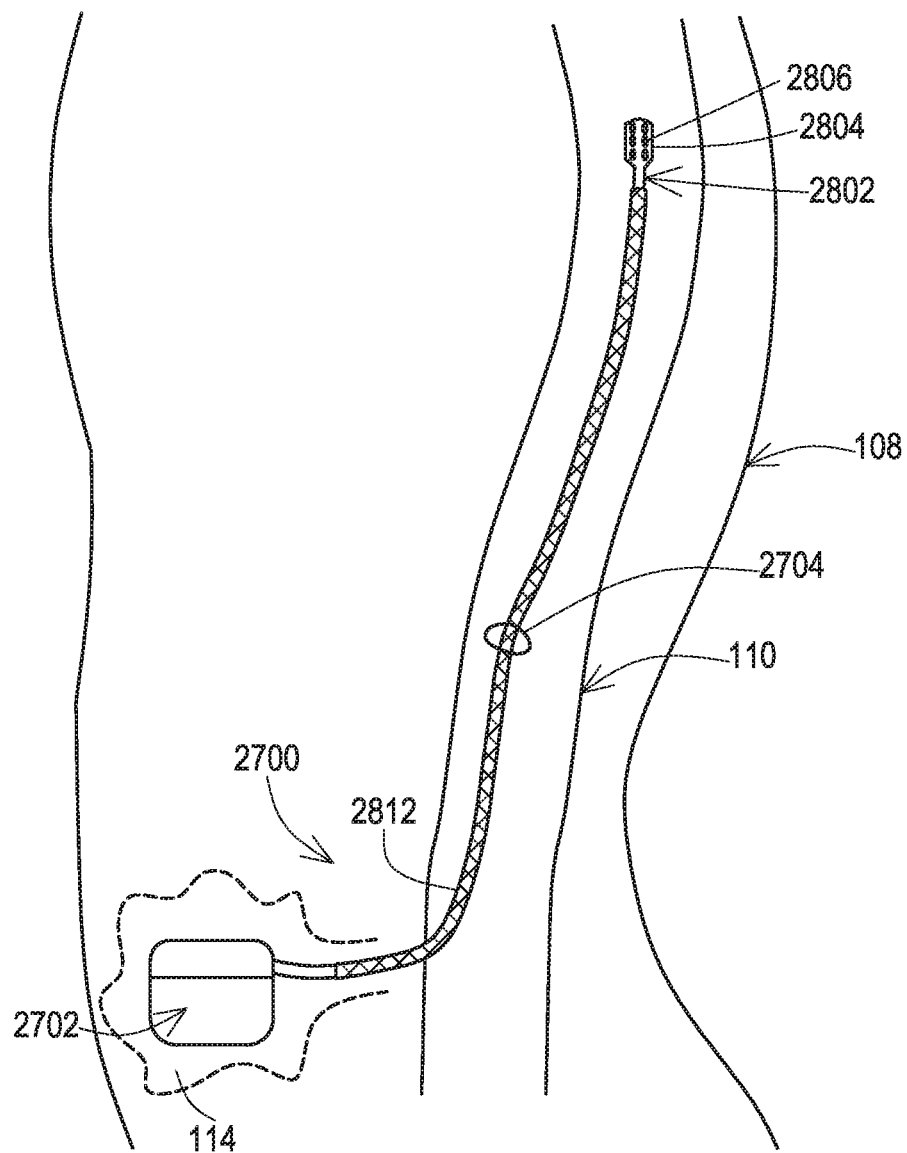
FIG. 27 shows an implantable medical system with the shielded sheath installed over a paddle lead.

FIG. 27 shows an implantable medical system 2700 that is implanted into the patient 108 and is similar to the implantable medical system of FIG. 2 except that the implantable medical system 2700 includes an implantable medical paddle lead 2802. The paddle lead 2802 has been implanted via an entry point 2704, typically created through a surgical procedure to create adequate space for the paddle portion 2806, and extends into the epidural space of the spine 110. The paddle lead 2802 includes a paddle portion 2804 that includes an array of electrodes 2806. The paddle lead 2802 is connected to an implantable medical stimulation device 2702 that is located in a pocket 114. A shielded sheath 2812 of the same construction as the prior embodiments discussed herein is positioned over the lead body of the paddle lead 2802.

Figure 28:
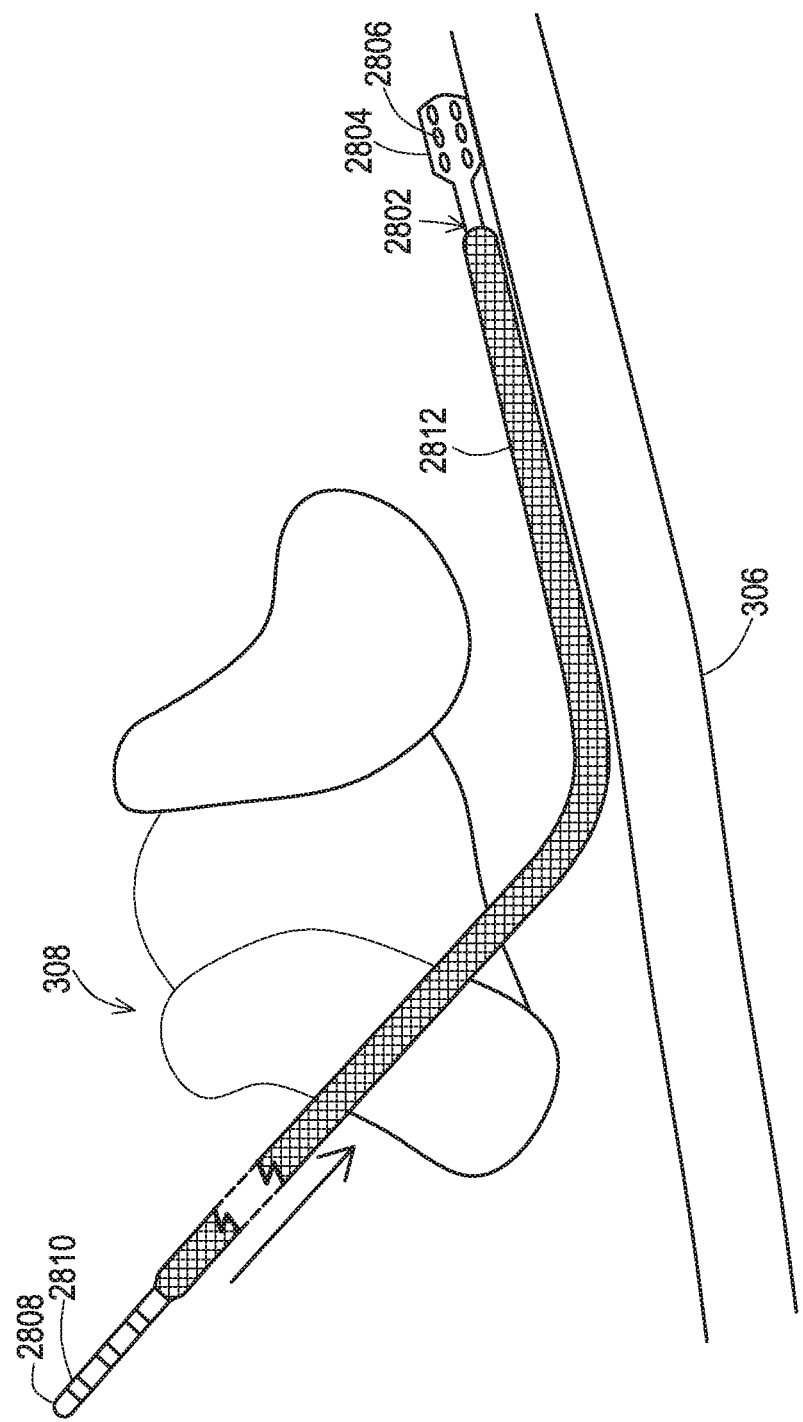
FIG. 28 shows the shielded sheath positioned over the paddle lead and being positioned within the epidural space.

As can be seen in FIG. 27 as well as in FIG. 28, the inside diameter of the shielded sheath 2812 is large enough to fit over the lead body. However, the width of the paddle portion 2804 is larger than the inside diameter of the shielded sheath 2812, which confines the position of the shielded sheath 2812 on the lead 2802. FIG. 28 further shows that the paddle lead 2802 and the shielded sheath 2812 are positioned within the epidural space by passing through the spinal structures 308 which may be further manipulated surgically when introducing the paddle portion 2804. Where the shielded sheath 2812 is being installed at the time of implantation of the lead 2802, various procedures are possible as discussed with reference to FIGS. 29 and 30. Where the lead 2802 is already implanted, then the shielded sheath 2812 may be added such as by a procedure shown in FIG. 31.

Figure 29:
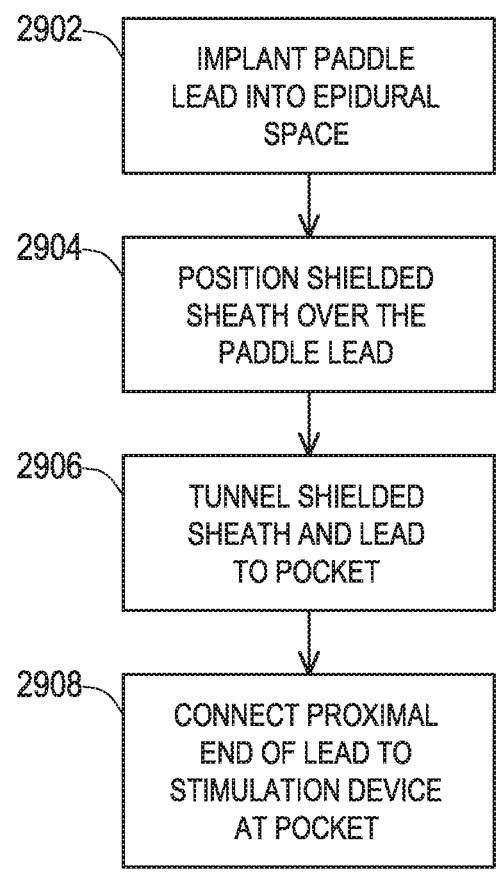
FIG. 29 shows a set of operations for one manner of implanting a shielded sheath and an implantable medical paddle lead.

The procedure of FIG. 29 begins by the paddle lead 2802 being implanted into the epidural space to place the paddle portion 2804 at the target site at operation 2902. The shielded sheath 2812 is then positioned over the paddle lead 2802 by feeding the proximal end of the paddle lead 2802 into the distal end of the shielded sheath and advancing the shielded sheath 2812 into the epidural space toward the paddle portion 2804 while the position of the lead 2802 is maintained at an operation 2904. Once the shielded sheath 2812 has been fully advanced onto the lead 2802, it may be desirable in some instances to also create a strain relief loop in the combination of the paddle lead 2802 and attached sheath 2812, such that the strain relief loop is shielded, at this intermediate location in the body of the patient near the entry to the epidural space. The proximal end of the lead 2802 and the shielded sheath 2812 positioned on the lead 2802 are then tunneled to the pocket 114 at an operation 2906. The proximal end 2808 of the lead 2802, which includes contacts 2810, is then connected to the stimulation device 2702 at an operation 2908. It may also be desirable in some instances to create a strain relief loop in the combination of the paddle lead 2802 and attached sheath 2812, such that the strain relief loop is shielded, at this location near the pocket 114 prior to connecting the proximal end 2808 to the device 2702.

An alternative procedure as shown in FIG. 30 begins by the shielded sheath 2812 being positioned over the paddle lead 2802. The proximal end of the paddle lead 2802 is fed into the distal end of the shielded sheath, and the shielded sheath 2812 is advanced toward the paddle portion 2804 prior to implantation of the lead 2802 at an operation 3002. The paddle lead 2802 and shielded sheath 218 are then implanted into the epidural space to place the paddle portion 2804 at the target site at operation 2902 at an operation 3004. With the shielded sheath 2812 fully advanced onto the lead 2802 and the combination of the shielded sheath 2812 and lead 2802 having been fully advanced to the stimulation site within the epidural space, it may be desirable in some instances to also create a strain relief loop in the combination of the paddle lead 2802 and attached sheath 2812, such that the strain relief loop is shielded, at this intermediate location in the body of the patient near the entry to the epidural space. The proximal end of the lead 2802 and the shielded sheath 2812 positioned on the lead 2802 are then tunneled to the pocket 114 at an operation 3006. The proximal end 2808 of the lead 2802, which includes contacts 2810, is then connected to the stimulation device 2702 at an operation 3008. It may also be desirable in some instances to create a strain relief loop in the combination of the paddle lead 2802 and attached sheath 2812, such that the strain relief loop is shielded, at this location near the pocket 114 prior to connecting the proximal end 2808 to the device 2702.

Figure 31B:
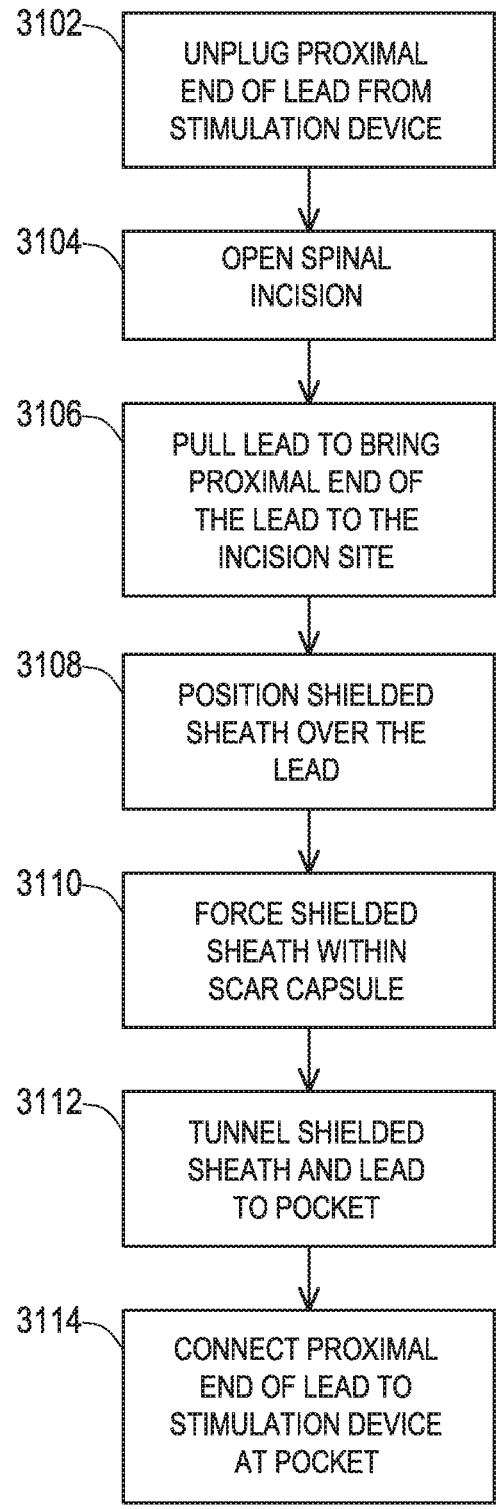

The procedures of FIG. 31A or 31B may be used to retrofit an implanted paddle lead 2802 with a shielded sheath 2812. The example of FIG. 31A may be implemented when a strain relief loop is either not already present or is present but not fibrosed and a strain relief loop is not desired upon placing the shielded sheath 2812 onto the lead 2802. This procedure begins by unplugging the proximal end 2808 of the lead 2802 from the stimulation device 2702 at an operation 3101. If there is a strain relief loop that is present but not fibrosed, then the lead may be gently pulled in the proximal direction to straighten the existing strain relief loop. The shielded sheath 2812 is then positioned over the paddle lead 2802 by feeding the exposed proximal end of the paddle lead 2802 into the distal end of the shielded sheath 2812 and advancing the shielded sheath 2812 into the epidural space toward the paddle portion 2804 while the position of the lead 2802 is maintained at an operation 3103. The shielded sheath 2812 may be forced into a scar capsule that has formed around the distal area of the lead present in the epidural space in order to fully advance the shielded sheath 2812 to the paddle portion 2804 at an operation 3105. The proximal end 2808 of the lead 2802, which includes contacts 2810, is then connected to the stimulation device 2702 at an operation 3107.

The example of FIG. 31B may be implemented when one or more strain relief loops are already present and fibrosed and/or are desired upon placing the shielded sheath 2812 onto the lead 2802. This procedure begins by unplugging the proximal end 2808 of the lead 2802 from the stimulation device 2702 at an operation 3102. The point of entry 2704, typically a surgical incision, of the lead 2802 into the epidural space may be reopened to access the lead 2802 at an operation 3104. The lead 2802 is then pulled from the pocket 114 to the point of entry 2704 to pull any existing strain relief loop straight and to gain access to the proximal end of the lead 2802 at an operation 3106. The shielded sheath 2812 is then positioned over the paddle lead 2802 by feeding the exposed proximal end of the paddle lead 2802 into the distal end of the shielded sheath and advancing the shielded sheath 2812 into the epidural space toward the paddle portion 2804 while the position of the lead 2802 is maintained at an operation 3108. The shielded sheath 2812 may be forced into a scar capsule that has formed around the distal area of the lead present in the epidural space in order to fully advance the shielded sheath 2812 to the paddle portion 2804 at an operation 3110. With the shielded sheath 2812 fully advanced onto the lead 2802, it may be desirable in some instances to also create a strain relief loop in the combination of the paddle lead 2802 and attached sheath 2812, such that the strain relief loop is shielded, at this intermediate location in the body of the patient near the entry to the epidural space. The proximal end of the lead 2802 and the shielded sheath 2812 positioned on the lead 2802 are then tunneled to the pocket 114 at an operation 3112. The proximal end 2808 of the lead 2802, which includes contacts 2810, is then connected to the stimulation device 2702 at an operation 3114. It may also be desirable in some instances to create a strain relief loop in the combination of the paddle lead 2802 and attached sheath 2812, such that the strain relief loop is shielded, at this location near the pocket 114 prior to connecting the proximal end 2808 to the device 2702.

Figure 32:
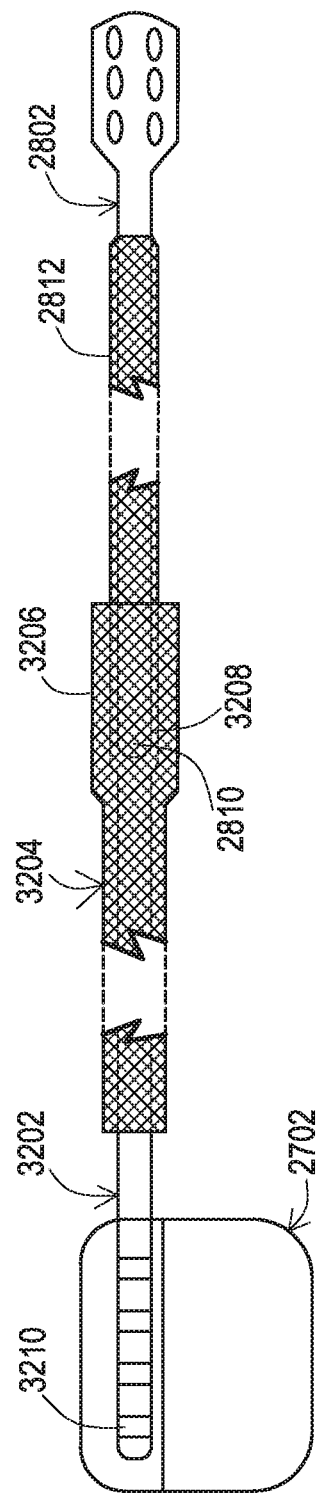
FIG. 32 shows an example of an implantable medical system that includes a lead extension, a paddle lead, and first and second shielded sheaths for the paddle lead and lead extension.

Should the paddle lead 2802 require an extension to reach the target site, FIG. 32 shows an example of such a configuration. Here, the proximal end 2810 of the lead 2802 has been connected to a distal connector block 3208 of connectors of a lead extension 3202. The shielded sheath 2812 is present on the lead 2802 while a second shielded sheath 3204 is present on the lead extension 3202. The second shielded sheath 3204 includes a portion 3206 that covers the distal connector block 3208 of the extension 3202. The proximal end of the lead 2802 includes contacts 3210 that are plugged into the stimulation device 2702.

The shielded sheath 2812 of FIGS. 27, 28, and 32 as well as the second shielded sheath 3204 may also include an electrical contact, such as the contact 2406 in FIG. 24, on the proximal end that can then establish a ground path with the stimulation device 2702. As another example, the electrical contact of the shielded sheath 2812 or second shielded sheath 3204 may have a first portion with a first diameter and a second portion and a second diameter that is smaller than the first, as shown in FIG. 25.

While embodiments have been particularly shown and described, it will be understood by those skilled in the art that various other changes in the form and details may be made therein without departing from the spirit and scope of the invention.

What is claimed is:

1. A method of shielding an implantable medical lead, comprising:
   providing a sheath that includes a shield layer;
   installing the sheath that includes the shield layer about an implantable medical lead between a proximal contact on the implantable medical lead and a distal electrode that are present on the implantable medical lead during the installation of the sheath; and
   anchoring the sheath to the implantable medical lead, wherein installing the sheath about the implantable medical lead comprises moving the sheath onto the implantable medical lead while the position of the implantable medical lead is maintained; and prior to moving the sheath onto the implantable medical lead, disconnecting the proximal contact of the implantable medical lead from a stimulation device present within a subcutaneous pocket, opening an incision near a stimulation site, and pulling the implantable medical lead from the subcutaneous pocket to a location of the incision.

2. The method of claim 1, further comprising after moving the sheath onto the implantable medical lead, tunneling the implantable medical lead and sheath to the subcutaneous pocket where the stimulation device is positioned and connecting the proximal contact of the implantable medical lead to the stimulation device.

3. A method of shielding an implantable medical paddle lead, comprising:

providing a sheath that includes a shield layer;

installing the sheath that includes the shield layer about an implantable medical lead between a proximal contact on the implantable medical lead and a paddle portion of the implantable medical paddle lead that are present on the implantable medical lead during the installation of the sheath, the sheath having an inner diameter that is smaller than a width of the paddle portion of the paddle lead but greater than a diameter of a remainder of the paddle lead;

confining the sheath to the implantable medical paddle lead, wherein installing the sheath about the implantable medical lead comprises moving the sheath onto the implantable medical lead while the position of the implantable medical lead is maintained; and prior to moving the sheath onto the implantable medical lead, disconnecting the proximal contact of the implantable medical lead from a stimulation device present within a subcutaneous pocket, opening an incision near a stimulation site, and pulling the implantable medical lead from the subcutaneous pocket to a location of the incision.

4. The method of claim 3, further comprising after moving the sheath onto the implantable medical lead, tunneling the implantable medical lead and sheath to the subcutaneous pocket where the stimulation device is positioned and connecting the proximal contact of the implantable medical lead to the stimulation device.

* * * * *